US010668280B2

(12) United States Patent
Milekovic et al.

(10) Patent No.: US 10,668,280 B2
(45) Date of Patent: Jun. 2, 2020

(54) TWO-PHASE CALIBRATION OF A NEUROPROSTHETIC SYSTEM

(71) Applicant: ECOLE POLYTECHNIQUE FEDERALE DE LAUSANNE (EPFL), Lausanne (CH)

(72) Inventors: Tomislav Milekovic, Geneva (CH); Marco Capogrosso, Pully (CH); Gregoire Courtine, Lausanne (CH); Eduardo Martin Moraud, Pully (CH); Fabien Wagner, Lausanne (CH); Jerome Gandar, Ecublens (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 677 days.

(21) Appl. No.: 15/340,728

(22) Filed: Nov. 1, 2016

(65) Prior Publication Data

US 2018/0117318 A1    May 3, 2018

(51) Int. Cl.
*A61N 1/36* (2006.01)
*A61B 5/0482* (2006.01)
(Continued)

(52) U.S. Cl.
CPC ........ *A61N 1/36003* (2013.01); *A61B 5/0075* (2013.01); *A61B 5/04001* (2013.01); *A61B 5/0476* (2013.01); *A61B 5/4836* (2013.01); *A61N 1/36062* (2017.08); *A61N 1/36067* (2013.01); *A61N 1/36139* (2013.01); *A61B 5/04842* (2013.01); *A61B 5/04845* (2013.01); *A61B 5/04847* (2013.01); *A61B 5/04888* (2013.01); *A61B 5/055* (2013.01); *A61F 2/54* (2013.01); *A61F 2/60* (2013.01); *A61N 1/0452* (2013.01); *A61N 1/0456* (2013.01);
(Continued)

(58) Field of Classification Search
CPC ... A61B 5/0482; A61B 5/4836; A61B 5/0476; A61B 2505/09; A61N 1/36; A61N 1/36003; A61N 1/36014
USPC ............................................. 607/48; 600/545
See application file for complete search history.

(56) References Cited

U.S. PATENT DOCUMENTS

2007/0004567 A1   1/2007   Shetty et al.
2011/0213266 A1*  9/2011   Williams ............. A61B 5/0482
                                                    600/545

FOREIGN PATENT DOCUMENTS

WO   2007047852 A2   4/2007

OTHER PUBLICATIONS

Sun, F. et al., "Sustained axon regeneration induced by co-deletion of PTEN and SOCS3," Nature, vol. 480, No. 7377, Dec. 15, 2011, Published Online Nov. 6, 2011, 12 pages.
(Continued)

*Primary Examiner* — Jon Eric C Morales
(74) *Attorney, Agent, or Firm* — McCoy Russell LLP

(57) ABSTRACT

Methods and systems are provided for triggering electrical stimulation of a spinal cord during execution of a motor event. In one example, a method comprises monitoring motor cortex activity while execution of a desired motor movement is attempted during a first mode where one or more nerve fibers are not stimulated, and during a second mode where the one or more nerve fibers are stimulated. Delivery timing of electrical stimulation may be closed-loop controlled based on current motor cortex activity and the motor cortex activity recorded previously during both the first and second modes.

17 Claims, 8 Drawing Sheets

(51) Int. Cl.
    A61B 5/00     (2006.01)
    A61B 5/04     (2006.01)
    A61B 5/0476   (2006.01)
    A61N 1/04     (2006.01)
    A61B 5/0484   (2006.01)
    A61N 1/05     (2006.01)
    A61F 2/54     (2006.01)
    A61B 5/0488   (2006.01)
    A61B 5/055    (2006.01)
    A61F 2/60     (2006.01)
(52) U.S. Cl.
    CPC .......... A61N 1/0476 (2013.01); A61N 1/0504
            (2013.01); A61N 1/0551 (2013.01); A61N
                                    1/36146 (2013.01)

(56) References Cited

OTHER PUBLICATIONS

Guyatt, G. et al., "The 6-minute walk: a new measure of exercise capacity in patients with chronic heart failure," Canadian Medical Association Journal, vol. 132, No. 8, Apr. 15, 1985, 5 pages.
Lovely, R. et al., "Effects of Training on the Recovery of Full-Weight-Bearing Stepping in the Adult Spinal Cat," Experimental Neurology, vol. 92, No. 2, May 1986, 15 pages.
Barbeau, H. et al., "Recovery of locomotion after chronic spinalization in the adult cat," Brain Research, vol. 412, No. 1, May 26, 1987, 12 pages.
Colgate, E. et al., "An Analysis of Contact Instability in Terms of Passive Physical Equivalents," Proceedings of the 1989 IEEE International Conference on Robotics and Automation, May 14, 1989, Scottsdale, Arizona, 6 pages.
Wernig, A. et al., "Laufband locomotion with body weight support improved walking in persons with severe spinal cord injuries," Paraplegia, vol. 30, No. 4, Apr. 1992, 10 pages.
Winter, D. et al., "An integrated EMG/biomechanical model of upper body balance and posture during human gait," Progress in Brain Research, vol. 97, Chapter 32, Available as Early as Jan. 1, 1993, 9 pages.
Wernig, A. et al., "Laufband Therapy Based on 'Rules of Spinal Locomotion' is Effective in Spinal Cord Injured Persons," European Journal of Neuroscience, vol. 7, No. 4, Apr. 1995, 7 pages.
Pratt, G. et al., "Stiffness Isn't Everything," Proceedings of the Fourth International Symposium on Experimental Robotics (ISER '95), Jun. 30, 1995, Stanford, California, 6 pages.
Basso, D. et al., "MASCIS Evaluation of Open Field Locomotor Scores: Effects of Experience and Teamwork on Reliability," Journal of Neurotrauma, vol. 13, No. 7, Jul. 1996, 17 pages.
Harkema, S. et al., "Human Lumbosacral Spinal Cord Interprets Loading During Stepping," Journal of Neurophysiology, vol. 77, No. 2, Feb. 1, 1997, 15 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, Sep. 22, 1997, 11 pages.
Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, 6 pages.
Hashtrudi-Zaad, K. et al., "On the Use of Local Force Feedback for Transparent Teleoperation," Proceedings of the 1999 IEEE International Conference on Robotics and Automation, May 10, 1999, Detroit, Michigan, 7 pages.
Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Aug. 1, 2000, Published Online Jul. 17, 2000, 2 pages.
Pratt, J. et al., "Series elastic actuators for high fidelity force control," Industrial Robot: An International Journal, vol. 29, No. 3, Available as Early as Jan. 1, 2002, 13 pages.
Steward, O. et al. "False Resurrections: Distinguishing Regenerated from Spared Axons in the Injured Central Nervous System," The Journal of Comparative Neurology, vol. 459, No. 1, Apr. 21, 2003, 8 pages.
Pearson, K., "Generating the walking gait: role of sensory feedback," Progress in Brain Research, vol. 143, Chapter 12, Published Online Nov. 28, 2003, 7 pages.
Bareyre, F. et al., "The injured spinal cord spontaneously forms a new intraspinal circuit in adult rats," Nature Neuroscience, vol. 7, No. 3, Mar. 2004, Published Online Feb. 15, 2004, 9 pages.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, Mar. 15, 2004, 11 pages.
Liu, J. et al., "Stimulation of the Parapyramidal Region of the Neonatal Rat Brain Stem Produces Locomotor-Like Activity Involving Spinal 5-HT7 and 5-HT2A Receptors," Journal of Neurophysiology, vol. 94, No. 2, Aug. 1, 2005, Published Online May 4, 2005, 13 pages.
Timoszyk, W. et al., "Hindlimb loading determines stepping quantity and quality following spinal cord transection," Brain Research, vol. 1050, No. 1-2, Jul. 19, 2005, Published Online Jun. 24, 2005, 10 pages.
Wernig, A., "'Ineffectiveness' of Automated Locomotor Training," Archives of Physical Medicine and Rehabilitation, vol. 86, No. 12, Dec. 2005, 2 pages.
Nessler, J. et al., "A Robotic Device for Studying Rodent Locomotion After Spinal Cord Injury," IEEE Transactions on Neural Systems and Rehabilitation Engineering, vol. 13, No. 4, Dec. 12, 2005, 10 pages.
Reinkensmeyer, D. et al., "Tools for understanding and optimizing robotic gait training," Journal of Rehabilitation Research & Development, vol. 43, No. 5, Aug. 2006, 14 pages.
Frey, M. et al., "A Novel Mechatronic Body Weight Support System," IEEE Transactions on Neural Systems and Rehabilitation Engineering, vol. 14, No. 3, Sep. 18, 2006, 11 pages.
Cai, L. et al., "Implications of Assist-As-Needed Robotic Step Training after a Complete Spinal Cord Injury on Intrinsic Strategies of Motor Learning," The Journal of Neuroscience, vol. 26, No. 41, Oct. 11, 2006, 5 pages.
Courtine, G. et al., "Can experiments in nonhuman primates expedite the translation of treatments for spinal cord injury in humans?," Nature Medicine, vol. 13, No. 5, May 2007, 13 pages.
Drew, T. et al., "Cortical mechanisms involved in visuomotor coordination during precision walking," Brain Research Reviews, vol. 57, No. 1, Jan. 2008, Published Online Aug. 22, 2007, 13 pages.
Edgerton, V. et al., "Training Locomotor Networks," Brain Research Reviews, vol. 57, No. 1, Jan. 2008, Published Online Sep. 16, 2007, 25 pages.
Kwakkel, G. et al., "Effects of Robot-assisted therapy on upper limb recovery after stroke: A Systematic Review," Neruorehabilitation and Neural Repair, vol. 22, No. 2, Mar. 2008, Published Online Sep. 17, 2007, 17 pages.
Courtine, G. et al., "Recovery of supraspinal control of stepping via indirect propriospinal relay connections after spinal cord injury," Nature Medicine, vol. 14, No. 1, Jan. 6, 2008, 6 pages.
Cowley, K. et al., "Propriospinal neurons are sufficient for bulbospinal transmission of the locomotor command signal in the neonatal rat spinal cord," The Journal of Physiology, vol. 586, No. 6, Mar. 15, 2008, Published Online Jan. 31, 2008, 13 pages.
Vallery, H. et al., "Compliant Actuation of Rehabilitation Robots," IEEE Robotics & Automation Magazine, vol. 15, No. 3, Sep. 12, 2008, 10 pages.
Edgerton, V. et al., "Robotic Training and Spinal Cord Plasticity," Brain Research Bulletin, vol. 78, No. 1, Jan. 15, 2009, Published Online Nov. 14, 2008, 19 pages.
Fuentes, R. et al., "Spinal Cord Stimulation Restores Locomotion in Animal Models of Parkinson's Disease," Science, vol. 323, No. 5921, Mar. 20, 2009, 14 pages.

(56) References Cited

OTHER PUBLICATIONS

Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Nov. 2009, Published Online Jul. 24, 2009, 5 pages.

Alto, L. et al., "Chemotropic Guidance Facilitates Axonal Regeneration and Synapse Formation after Spinal Cord Injury," Nature Neuroscience, vol. 12, No. 9, Sep. 2009, Published Online Aug. 2, 2009, 22 pages.

Courtine, G. et al., "Transformation of nonfunctional spinal circuits into functional states after the loss of brain input," Nature Neuroscience, vol. 12, No. 10, Oct. 2009, Published Online Sep. 20, 2009, 12 pages.

Hagglund, M. et al., "Activation of groups of excitatory neurons in the mammalian spinal cord or hindbrain evokes locomotion," Nature Neuroscience, vol. 13, No. 2, Feb. 2010, Published Online Jan. 17, 2010, 8 pages.

Wessels, M. et al., "Body Weight-Supported Gait Training for Restoration of Walking in People With an Incomplete Spinal Cord Injury: A Systematic Review," Journal of Rehabilitation Medicine, vol. 42, No. 6, Jun. 2010, 7 pages.

Zorner, B. et al., "Profiling locomotor recovery: comprehensive quantification of impairments after CNS damage in rodents," Nature Methods, vol. 7, No. 9, Sep. 2010, Published Online Aug. 15, 2010, 11 pages.

Ada, L. et al., "Mechanically assisted walking with body weight support results in more independent walking than assisted overground walking in non-ambulatory patients early after stroke: a systematic review," Journal of Physiotherapy, vol. 56, No. 3, Sep. 2010, 9 pages.

Duschau-Wicke, A. et al., "Patient-cooperative control increases active participation of individuals with SCI during robot-aided gait training," Journal of NeuroEngineering and Rehabilitation, vol. 7, No. 43, Sep. 10, 2010, 13 pages.

Rosenzweig, E. et al., "Extensive Spontaneous Plasticity of Corticospinal Projections After Primate Spinal Cord Injury," Nature Neuroscience, vol. 13, No. 12, Dec. 2010, Published Online Nov. 14, 2010, 19 pages.

Hidler, J. et al., "ZeroG: Overground gait and balance training system," Journal of Rehabilitation Research & Development, vol. 48, No. 4, Available as Early as Jan. 1, 2011, 12 pages.

Musselman, K. et al., "Spinal Cord Injury Functional Ambulation Profile: A New Measure of Walking Ability," Neurorehabilitation and Neural Repair, vol. 25, No. 3, Mar. 2011, Published Online Feb. 25, 2011, 9 pages.

Harkema, S. et al., "Effect of Epidural stimulation of the lumbosacral spinal cord on voluntary movement, standing, and assisted stepping after motor complete paraplegia: a case study," The Lancet, vol. 377, No. 9781, Jun. 4, 2011, Published Online May 20, 2011, 17 pages.

Wirz, M. et al., "Effectiveness of automated locomotor training in patients with acute incomplete spinal cord injury: A randomized controlled multicenter trial," BMC Neurology, vol. 11, No. 60, May 27, 2011, 5 pages.

Musienko, P. et al., "Controlling specific locomotor behaviors through multidimensional monoaminergic modulation of spinal circuitries," The Journal of Neuroscience, vol. 31, No. 25, Jun. 22, 2011, 32 pages.

Musienko, P. et al. "Multi-system neurorehabilitative strategies to restore motor functions following severe spinal cord injury," Experimental Neurology, vol. 235, No. 1, May 2012, Published Online Sep. 7, 2011, 10 pages.

Gilja, V. et al., "A high-performance neural prosthesis enabled by control algorithm design," Nature Neuroscience, vol. 15, No. 12, Dec. 2012, Published Online Nov. 18, 2012, 7 pages.

Wenger, N. et al., "Closed-loop neuromodulation of spinal sensorimotor circuits controls refined locomotion after complete spinal cord injury," Science Translational Medicine, vol. 6, No. 255, Sep. 24, 2014, 10 pages.

Wenger, N. et al., "Supplementary Materials for Closed-loop neuromodulation of spinal sensorimotor circuits controls refined locomotion after complete spinal cord injury," Science Translational Medicine, vol. 6, No. 255, Sep. 24, 2014, 14 pages.

Jarosiewicz, B. et al., "Virtual typing by people with tetraplegia using a self-calibrating intracortical brain-computer interface," Science Translational Medicine, vol. 7, No. 313, Nov. 11, 2015, 11 pages.

Jarosiewicz, B. et al., "Supplementary Materials for Virtual typing by people with tetraplegia using a self-calibrating intracortical brain-computer interface," Science Translational Medicine, vol. 7, No. 313, Nov. 11, 2015, 26 pages.

Capogrosso, M. et al., "A brain-spine interface alleviating gait deficits after spinal cord injury in primates," Nature, vol. 539, No. 7628, Nov. 10, 2016, Published Online Nov. 9, 2016, 23 pages.

\* cited by examiner

TWO-PHASE CALIBRATION OF A NEUROPROSTHETIC SYSTEM

FIELD

The present description relates generally to methods and systems for calibrating a neuroprosthetic system.

BACKGROUND/SUMMARY

Neuroprosthetic devices have been developed to alleviate deficits in motor, sensory and cognitive functions. Cochlear implants for example, one of the inaugural neuroprosthetics, are now widely used among those hard of hearing. In recent years, neuroprosthetic devices targeted towards movement restoration have seen considerable advances. For example, one approach aimed at restoring locomotion in patients suffering from spinal cord injury (SCI) involves electrically simulating the spinal cord during voluntary and/or assisted stepping. The approach typically involves delivering epidural electrical spinal cord stimulation (EES) based on brain activity monitored by a neurosensor, such as an electrode array. In this way, application of the electrical stimulation may be closed-loop controlled responsive to changes in brain activity.

The effectiveness of neuroprosthetic stimulation in restoring motor movement functionality may depend on its delivery timing (e.g., when it is delivered during execution of the motor movement). In the absence of a spinal cord injury, brain generated movement commands may be transmitted to appropriate muscles tasked with carrying out the desired movement. However, due to the spinal cord injury, transmission of such motor movement commands may be interrupted. Thus, the calibration of the neuroprosthetic may involve learning the unique brain activity patterns associated with the motor movement command of interest to be able to detect when the motor movement command is being generated. Delivery of the stimulation can then be coordinated with the brain commanded motor movement to mimic how the motor movement command would ordinarily be communicated to the muscles by the spinal cord absent injury. Calibrating the neuroprosthetic therefore, typically involves determining when to provide the stimulation to achieve optimal motor recovery.

Thus, during calibration, brain activity may be monitored while the motor movement (e.g., stepping) is repeatedly attempted. For example, motor cortex activity may be monitored following a prompt to perform the motor movement. In one example, the prompt may include operating an external device (e.g., harness and treadmill in the example of stepping) to cue and/or facilitate a motor task. However, it should be appreciated that the movement does not need to be executed in order to monitor brain activity. That is, brain activity monitored during an attempted movement may be similar to activity observed during volitionally executed movements. Thus, execution of the motor movement is not required during calibration of the neuroprosthetic system. Furthermore, stimulation may not be triggered by brain activity associated with non-volitional movements (e.g., passive or simulated movements). The recorded brain activity is then time-aligned with the prompts to attempt to perform motor movements in order to learn the neural activity patterns associated with the appropriate delivery timing of the stimulation. After calibration, electrical stimulation can be triggered in a closed-loop manner by comparing current brain activity to the brain activity patterns associated with the desired delivery timing of the stimulation. In this way, temporal acuity of stimulation may be improved.

However, the inventors herein have recognized potential issues with such systems. As one example, stimulating the spinal cord may affect neural activity in the brain. Thus, the neural activity recorded during and/or after stimulating the spinal cord may be different than it would otherwise be in the absence of the electrical stimulation. Such changes in neural activity, when not accounted for in the calibration of the neuroprosthetic device, can lead to aberrant stimulation. That is, due to the effects of the electrical stimulation on neural activity, stimulation of the spinal cord may be triggered when it is not desired, and/or not triggered when desired. When the stimulation is mis-applied, the effectiveness of the neuroprosthetic in restoring motor movement may be reduced. For example, the neural activity resulting from electrical stimulation of the spinal cord may closely resemble neural activity associated with a desired time to deliver the electrical stimulation. As such, the neural activity resulting from electrical stimulation of the spinal cord can be misidentified during closed loop control as a desired time to stimulate, leading to over-stimulation of the spinal cord. Thus, closed-loop control schemes may improperly identify neural activity resulting from the electrical stimulation as a desired time to stimulate the spinal cord. Such errors in the delivery timing of the electrical stimulation may prohibit and/or reduce the restoration of motor movements.

In one example, at least some of the issues described above may be at least partially addressed by a method for, during a first mode, monitoring motor cortex activity while not stimulating any nerve fibers, and during a second mode, stimulating the one or more nerve fibers, and monitoring motor cortex activity during and after stimulating the one or more nerve fibers. The method may further comprise generating a model that predicts motor movement commands based on the motor cortex activity monitored during both the first and second modes. In this way, the way in which the motor cortex responds to electrical stimulation may be learned and accounted for during closed-loop control of spinal cord stimulation. As such, undesirable stimulation events that would be triggered when not accounting for the effects of stimulation on neural activity, may be reduced. Furthermore, the number of stimulation events that would not have been triggered at the appropriate times when not accounting for the effects of stimulation on neural activity, may be reduced as well.

In some examples, the method may comprise executing the first mode before the second mode. After executing the first mode, an initial motor cortex activity profile may be generated based on the motor cortex activity monitored during the first mode. Then, a new motor cortex activity profile may be generated based on the motor cortex activity monitored both during the first and the second mode. In particular, differences in neural activity between the first and second modes may be the result of the electrical stimulation provided in the second mode. Thus, the new motor cortex activity profile is calibrated to interpret neural activity from both modes, in the presence and absence of stimulation, at the times that would be appropriate to trigger the stimulation as being the correct times appropriate to trigger the stimulation.

Thus, the method may comprise learning a neural response signal that results from stimulating the spinal cord. By modifying the motor cortex activity profile based on the neural response signal, the accuracy of predictions of future motor cortex activity patterns may be increased. In particular, when electrical stimulation is applied to the spinal cord, neural activity resulting from the electrical stimulation may be more accurately anticipated and accounted for in the motor cortex activity profile. By accounting for such changes in motor cortex activity resulting from electrical stimulation of the spinal cord, delivery of the electrical stimulation may be more effectively timed to restore motor movement.

As another example, a method may comprise, while monitoring motor cortex activity during attempted execution of a desired motor movement, electrically stimulating a nerve fiber at a desired instance following a motor movement command. The method may additionally comprise, while inducing execution of the desired motor movement, electrically stimulating the nerve fiber under closed-loop feedback control based on current motor cortex activity and the monitored motor cortex activity. The motor movement command may be generated by a motor cortex and may command for execution of the desired motor movement.

In yet another example, a neuroprosthetic system may comprise a neurosensor for monitoring neural activity, an electrical stimulator for delivering electrical stimulation to one or more nerve fibers, a controller in communication with the neurosensor and electrical stimulator including computer readable instruction stored in non-transitory memory for triggering electrical stimulation events based on neural activity recordings received from the neurosensor, generating a set of computer readable instructions using neural activity profile based on neural activity monitored during one or more repetitions of a motor event stored in the non-transitory memory, electrically stimulating a nerve fiber during one or more repetitions of that motor event, generating another set of computer readable instructions using neural activity profile based on neural activity monitored during the one or more repetitions in the absence of stimulation and one of more repetitions in the presence of stimulation, and replacing the prior set of instructions stored in the non-transitory memory with the new set of instructions.

In this way, by accounting for how the brain responds to electrical stimulation of the spinal cord, undesirable stimulations of the spinal cord which may impede restoration of motor movement may be reduced. Thus, neural responses resulting from electrical stimulation of the spinal cord that occur during the times when the stimulation is not desired are learned to not be associated with a desired time to stimulate the spinal cord, and unintended spinal cord stimulations may be avoided. Furthermore, neural responses observed in the presence of electrical stimulation of the spinal cord during the times that are appropriate to trigger the stimulation are learned to be associated with a desired time to stimulate the spinal cord, and not triggering spinal cord stimulations at the appropriate time may also be avoided. Said another way, spinal cord simulations may be more accurately timed to coincide with brain generated motor movement commands to more optimally promote execution of the motor movement.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1A:
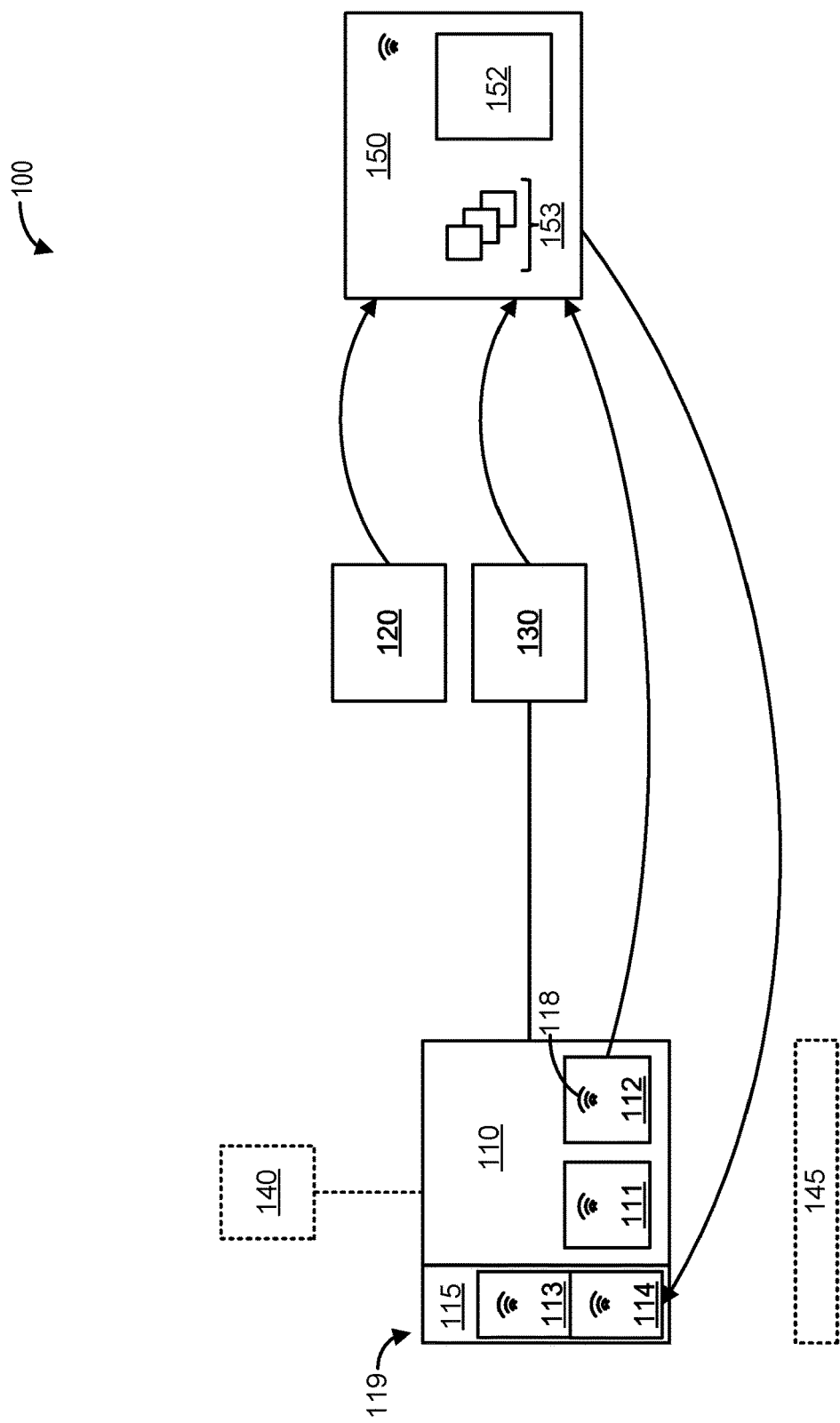
FIG. 1A shows a schematic diagram of an example neuroprosthetic system, in accordance with an embodiment of the present disclosure.

The following description relates to systems and methods for calibrating a neuroprosthetic system, an example of which is shown in FIG. 1A. In the depicted embodiment, the neuroprosthetic system may comprise a neurosensor for recording brain activity, and a stimulator for providing external sensory stimulation to the central nervous system. For example, the stimulator may provide one or more of visual, auditory, tactile, or electrical stimulation. Further, the neuroprosthetic system may comprise a controller in communication with the neurosensor and stimulator for triggering stimulation by the stimulator based on input from the neurosensor. The controller may determine when to deliver the stimulation based on current neural activity and an algorithm that takes as an input the neural activity data, and then through one or more internal calculations, generates as an output, a likelihood that the motor cortex is generating a motor movement command. In this way, the controller may regulate the delivery of the stimulation in a closed-loop manner, as described in the example method of FIG. 2.

However, stimulation provided by the stimulator may affect brain activity. Specifically, the brain may respond to input received from the stimulator, as shown in the example graph of FIG. 5. In some examples, the brain's response to a stimulation event may trigger the controller to stimulate again, leading to over-stimulation. In particular, when the brain's response to the stimulation is not accounted for in the calibration routine, it may be misidentified as a desired time to stimulate. In other examples, the brain's response to stimulation may cause the controller to omit the stimulation at a time when it would have been appropriate. In particular, when the brain's response to the stimulation is not accounted for, the stimulation may be omitted at the time it would have otherwise been triggered.

Thus, during calibration of the neuroprosthetic system, the stimulator may be triggered to deliver stimulation, and the response of brain to the stimulation may be learned by monitoring the neural activity during and after the stimulation, as described in the example method of FIG. 4. By learning the brain's response to the stimulation during the calibration, future brain responses to the stimulation may be more accurately anticipated, and the effectiveness of the neuroprosthetic in restoring central nervous system function may be increased.

As one example, the calibration of the neuroprosthetic system described herein, may be applied to a neuroprosthetic system aimed at restoring motor movement to individuals suffering from one or more of spinal cord injury, brain injury, neurological and/or neuromuscular disease, etc. In the particular example of spinal cord injury, the neurosensor may comprise an epidural electrical spinal cord stimulator (EES). To calibrate such a neuroprosthetic system, brain activity may be monitored and recorded during attempted execution of a motor movement, such as stepping. If the movement cannot be partially or completely executed, the subject can be cued to attempt to perform the movement. Such movement attempts may elicit systematic brain activity, i.e. the brain activity elicited during each movement attempt will be similar. Such brain activity may resemble brain activity that would have been observed if the motor movement had actually occurred in examples where the individual is unable to perform the movement. Execution or attempts of the movements may be aided by positioning the participant in the appropriate positions, e.g. using a harness or an exoskeleton.

During a first phase of the calibration, execution of the motor movement may be attempted, and stimulation may not be delivered to the spinal cord. The brain activity may be monitored during the first phase to detect a brain generated motor movement command that commands for a desired motor movement. In particular, a neural activity pattern that represents the brain generated motor movement command may be learned. A desired instance to deliver stimulation may then be determined based on the identified brain generated motor movement command. That is, the desired instance may be determined relative to the timing of the generation of the motor movement command. Then, during a second phase of the calibration, stimulation may be delivered at the desired instance, and the resulting neural response to the electrical stimulation may be learned. Thus, a model predicting movements from neural responses both during the absence and presence of stimulation may be generated based on the two phases of the calibration. In this way, neural responses to the delivered electrical stimulation may be accounted for during motor recovery therapy. As such, the accuracy of the electrical stimulation delivery timing may be increased, and over-stimulation of the spinal cord may be reduced.

It should be appreciated that while sections of this disclosure may focus on neuroprosthetic systems involved in motor movement restoration, the systems and methods disclosed herein may be used in other neuroprosthetic systems without departing from the scope of the disclosure. In particular, it should be noted that portions of the present disclosure may focus on a neuroprosthetic system including an electrical stimulator that delivers electrical stimulation to a spinal cord. However, such description is provided merely to show one such example of how the methods described herein may be applied to a neuroprosthetic system. Thus, the present disclosure relates to systems and methods for calibration of a neuroprosthetic system involving one or more of visual, auditory, tactile, electrical, or other form of stimulator that delivers sensory stimulation directly and/or indirectly to the central nervous system.

Turning to the figures, FIG. 1A shows a block diagram of an example neuroprosthetic system 100. The neuroprosthetic system 100 includes a stimulation device 111 and a neurosensor 112. In the depicted embodiment, stimulation device 111 provides external sensory input to the central nervous system of a user 110. For example, the stimulation device 111 may provide one or more of auditory, visual, tactile, thermal, chemical, optical, olfactory, gustatory, and electrical stimulation. As such, the stimulation device 111 may comprise one or more of a speaker, visual display screen, haptic stimulation inducer, heater, pharmaceutical delivery system, laser activating genetically modified chemical compounds, gas delivery system, taste delivery system and electrical stimulation device. In another embodiment, stimulation device 111 may provide stimulatory input to another body part, such as the bladder, eyes, ears, heart, muscles, bowels, etc. In yet another embodiment, stimulation device 111 may provide input to a robotic or mechanical device.

In examples where the stimulation device 111 delivers electrical stimulation, the stimulation device 111 may be coupled to the user 110 and may provide electrical stimulation to the spinal cord of user 110. In particular, the stimulation device 111 may comprise a pulse generator electrically coupled to an array of electrodes. The electrodes may be placed epidurally or subdurally. The array of electrodes of the stimulation device 111 may be implanted under vertebras L1-L4, and in particular, over the dorsal side of spinal segments ranging from L1 to S5, for enabling and/or facilitating movement of the lower limbs. Alternatively, the array of electrodes of the stimulation device 111 may be implanted under vertebras C2-T1, and, in particular, over the dorsal side of spinal segments ranging from C3 to T1, for enabling and/or facilitating movement of the upper limbs.

In particular, the neuroprosthetic system 100 may be used to provide stimulation (e.g., electrical stimulation) to the spinal cord in response to neural activity in the motor cortex of user 110 in order to restore and/or control voluntary movement of the limbs and/or extremities, such as the legs, arms, hands, etc. In another example, the neuroprosthetic system 100 may be used to control a bionic robotic prosthetic.

Optionally, in the depicted embodiment, a motor movement eliciting device 145 may be used to prompt user 110 to attempt movement. For example, the motor movement eliciting device 145 may comprise a treadmill that prompts locomotion from user 110. However, the motor movement eliciting device 145 may be another device that prompts user 110 to attempt a different motor task. For example, eliciting device 145 may be a visual and/or auditory cue. In this way, user 110 is prompted to attempt a motor task so that volitional neural activity may be recorded, even in the absence of voluntary motor behavior. Further, movement eliciting device 145 may be used following spinal cord stimulation to facilitate locomotion of user 110 in response to stimulation. Additionally or alternatively, user 110 may be optionally coupled to an assistance device 140 to assist in execution of the motor movement by residual voluntary control of user 110 or elicited by the eliciting device 145. In one example, assistance device 140 may be one or more of a robotic assistance device, a harness, a walker, physical assistance, an over-ground body weight support system, etc. Thus, in examples where the eliciting device 145 comprises a treadmill, the assistance device 140 may comprise a chest harness that holds the user 110 in an upright position to elicit neural activity associated with locomotion and/or facilitate locomotion following stimulation.

As user 110 is attempting and/or engaged in a motor task, data congruent with user's attempts to move (e.g., neural activity recordings from neurosensor 112) are sent to the controller 150. If user 110 is capable of executing, or partially executing, movements (e.g., engage some or all of the muscles involved in the attempted movement), the data may come in a form of kinematic data from one or more motion sensors, including a motion capture system 120, a force place, an electromyogram recording system 130, a system of accelerometers affixed to user 110, etc. Controller 150 may also receive data from devices that instruct the user 110 to move in a time locked coordinated way, such as speakers delivering auditory cues, video screen or lights delivering visual cues, electrical stimulators or any other device capable of delivering cues to user 110. By recording neural activity following a prompt for the motor task, modulation of the user's neural responses in response to attempting the motor task may be used by detectors (e.g., an algorithm) of controller 150 to establish a model that maps neural activity to motor task attempts, which may be used to detect motor task attempts from neural activity. In this way, the motor task is employed to detect neural activity congruent with volitional movement execution.

During kinematic activity (e.g., motor movement), kinematic data for user 110 is relayed to controller 150. Controller 150 receives kinematic activity signals from one or more of a motion capture system 120 and an electromyogram 130. The motion capture system 120 records physical movements of the user 110. For example, the motion capture system 120 may comprise one or more of a video camera, an inertial measurement unit (IMU), an accelerometer, a gyroscope, a pressure sensor, a force sensor, an ultrasound detector, and an infrared sensor. The motion capture system 120 may relay positional and/or movement data to the controller 150 via a wired and/or wireless connection. The movement data may comprise data encoding recorded physical movements of the user 110. In examples where user 110 is walking, the motion capture system 120 records phases of the gait, such as stance and swing phases, and specific gait events such as foot off, and foot strike. Thus, the motion capture system 120 is used to record events and phases of the movement performed and/or aided by the movement eliciting device 145. However, in other examples, physical movement of the user 110 may be measured via the electromyogram 130. In still further examples, physical movement of the user 110 may be measured via both the electromyogram 130 and the motion capture system 120. Thus, when included in the neuroprosthetic system 100, the electromyogram 130 may be in communication with the controller 150 via a wired and/or wireless connection for transmitting movement data to the controller 150. In the description herein, the movement data may also be referred to as kinematic activity data. Electromyogram 130 is coupled to user 110 and records electrical activity at the muscles, which may be used to infer movement. Muscle activity during a motor task is then wirelessly transmitted from electromyogram 130 to controller 150. In another embodiment, electromyogram 130 may be wired to controller 150 in order to relay muscle activity recordings. The motion capture system 120 records kinematic activity of user 110 during treadmill 145 use or over-ground walking. For example, motion capture system 120 may be a video recording of user 110 performing the motor task. In this way, output signals for both motor cortex activity and kinetic activity are relayed to controller 150 during the motor task by neurosensor 112 and one or more of motion capture system 120 and electromyogram 130, respectively.

Further, controller 150 may be in wireless communication with the neurosensor 112 for receiving neural activity data therefrom. The neural activity data may comprise voltage output from the brain (e.g., motor cortex) of user 110, in examples where the neurosensor 112 comprises a microelectrode array. In such examples, neurosensor 112 may be coupled to user 110 and may wirelessly transmit neural activity data (e.g., motor cortex activity) to controller 150 via wireless signal 118. However, in other examples, neurosensor 112 may be an electroencephalogram (EEG) or an intracranial electroencephalogram (iEEG). In yet further examples, neurosensor 112 may be a functional magnetic resonance imager (fMRI), electrocorticogram, near infra-red spectroscopy imaging device (NIRS), glass pipette electrode, one or two photon excitation imaging with calcium indicators, neural activity recorded using voltage sensitive dyes, neural dust, tetrode array, wire electrodes, patch clamping, etc. In examples where the neurosensor 112 comprises a microelectrode array, the neurosensor 112 may be coupled to the motor cortex for monitoring motor cortex activity. Thus, the neurosensor 112 may transmit neural activity data, corresponding to electrical output from the motor cortex, to the controller 150. En route to the controller 150, the neural activity data measured by the neurosensor 112 may be digitized and packaged by a signal processor and transmitted to the controller 150 over a local internet connection, such as via an Ethernet cable, via a standard communication protocol such as user datagram protocol (UDP). However, it should be appreciated that other data transmission protocols (e.g., software) and transmission devices (e.g., hardware) may be implemented without departing from the scope of the present disclosure.

Neural and kinematic activity data is processed by an algorithm 153 of controller 150 to generate a model of currently executed motor movements using motor cortex activity. Thus, the neural activity data and kinematic activity data, is time synchronized to map the neural activity data to the corresponding kinematic activity data. In this way, neural activity patterns generated during execution of the motor movement may be identified by synchronizing the neural activity data with the kinematic activity data. The model of attempted motor movements using motor cortex activity created by an algorithm 153 is then used to adjust a stimulation protocol employed by a stimulation device system 119 to trigger spinal cord stimulation.

In particular, controller 150 includes a decoder (e.g., algorithm) that processes neural activity data. Specifically, the decoder may perform one or more mathematical operations on the neural activity data as described in greater detail below with reference to FIG. 3 to determine a likelihood that a motor movement command is being generated by the motor cortex. For example, the decoder may project the neural activity from a larger multidimensional space into a smaller dimensional space. The decoder may be calibrated based on neural activity monitored during both the presence and absence of stimulation when the motor movement command is generated by the motor cortex.

FIG. 1A further shows a controller 150. Controller 150 may be communicatively coupled to various components of neuroprosthetic system 100 to carry out the control routines and actions described herein. For example, as shown in FIG. 1A, controller 150 may be a computer, including a processor unit, input/output ports, an electronic storage medium for executable programs and calibration values, random access memory, keep alive memory, and a data bus. Further, controller 150 may take the form of one or more personal computers, server computers, tablet computers, network computing devices, mobile computing devices, mobile communication devices (for example, smart phone, smart watch, etc.), and/or other computing devices. As depicted, controller 150 may receive input from a plurality of sensors, which may include user inputs and/or sensors (such as neural activity, muscle activity, etc.) and others. Controller 150 may include one or more algorithms 153 for analyzing various signals received by controller 150, including motor activity, muscle activity, and neural responses. Additionally, controller 150 may include an interface 152. Furthermore, controller 150 may communicate with various components of stimulation device system 119, which may include interface module 113 that is coupled to stimulation programmer 114. In some examples, the storage medium (e.g., memory) may be programmed with computer readable data representing instructions executable by the processor for performing the methods described below as well as other variants that are anticipated but not specifically listed.

Additionally, user 110 may be physically coupled to stimulation device system 119. Stimulation device system 119 includes an interface module 113, stimulation device 111, and a stimulation programmer 114. In one embodiment, interface module 113 and stimulation programmer 114 may be contained within a single housing. In another embodiment, interface module 113 and stimulation programmer 114 may be housed in separate units. Additionally, interface module 113 and stimulation programmer 114 may be paired with a garment 115, which is worn by user 110. In one example, garment 115 may be a jacket. In yet another embodiment, interface module 113, stimulation programmer 114, and stimulation device 111 may be contained within a single housing and implanted subcutaneously. Interface module 113 receives output for stimulation parameters for a stimulation device 111 from controller 150 and relays the stimulation parameters to stimulation programmer 114. In one example, interface module 113 wirelessly receives Bluetooth signals from controller 150 and relays stimulation commands to stimulation programmer 114 via infrared. Stimulation commands are then transmitted from stimulation programmer 114 to stimulation device 111. In one example, stimulation programmer 114 relays signals to stimulation device 111 via transcutaneous telemetry. In the depicted embodiment, stimulation device 111 is an implantable pulse generator that electrically stimulates the spinal cord of user 110 to control movement. For example, stimulation device 111 may be an implantable pulse generator that consists of an array of electrodes positioned epidurally or subdurally. Stimulation from the implantable pulse generator may be provided by passing current through one or more of the electrodes of the array for a duration. In one example, a stimulation event may consist of a burst of pulses from the implantable pulse generator. In another example, a stimulation event may consist of one or more of a single stimulation pulse. The single stimulation pulse may be a biphasic pulse, where the first pulse (e.g., phase) is a square wave pulse and the second pulse is an exponential decay pulse. For example, the stimulation event may be a 210 ms 50 Hz burst, which consists of nine single biphasic stimulation pulses of 50-2000 microseconds delivered 25 ms apart. In another embodiment, stimulation device 111 may employ photo- or vibrational stimulation of the spinal cord.

Figure 1B:
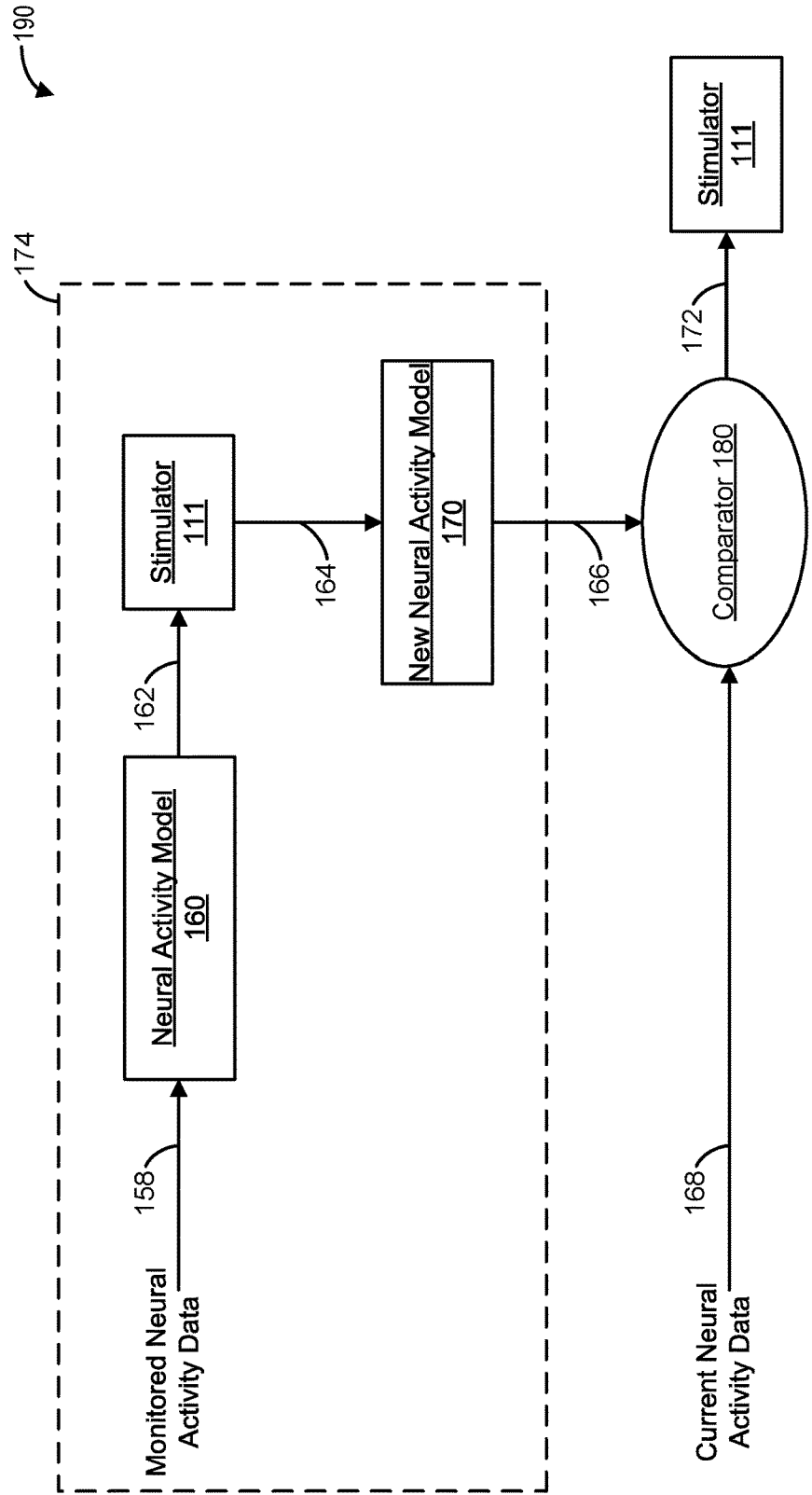
FIG. 1B shows a block diagram of a first example control routine for closed-loop controlling delivery of stimulation of stimulator of a neuroprosthetic system, such as the example neuroprosthetic system of FIG. 1A, in accordance with an embodiment of the present disclosure.

Continuing to FIG. 1B, it shows an example schematic 190 of a first control scheme for regulating delivery of stimulation provided by a stimulator of a neuroprosthetic. In particular, the stimulation scheduling control scheme provided in FIG. 1B may be used in the neuroprosthetic system 100 described above in FIG. 1A, for example. Neural activity data 158 may be monitored via a neurosensor (e.g., neurosensor 112 described above in FIG. 1A) while a user attempts to execute and/or partially executes a motor movement. The neural activity data may be used to identify when it is desired to deliver electrical stimulation based on neural activity. Thus, neural activity may be monitored while execution of the desired motor movement is attempted to identify a neural activity pattern that represents a command for execution of the desired motor movement. In some examples, a motor movement command model 160 may be generated to describe the commands for execution of the desired motor movement given the neural activity pattern. In particular, the motor movement command model 160 may predict motor movement commands that would lead to execution of the motor movement based on the neural activity data 158. After calibration, the motor movement command model may take processed neural activity data as input, and may output a likelihood that the motor movement command is or has been generated. In particular, one or more algorithms included in a controller (e.g., controller 150 described above with reference to FIG. 1A) may process the neural activity data received from the neurosensor, and the processed neural activity data may then be compared to the motor movement command model. Thus, a likelihood that a motor movement command is being generated is determined by comparing the processed neural activity data to the motor movement command model.

Further, the neural activity data 158 may be mapped to the motor movement to determine the neural activity patterns present at various phases of the motor movement. In particular, the brain generated motor movement command that commands for execution of a desired motor movement may be identified based on the neural activity patterns. More specifically, the motor movement command may comprise a particular pattern of motor cortex neural activity. Thus, the pattern of neural activity representing the motor movement command may be learned and/or identified by monitoring neural activity during attempted execution of the motor movement.

In another embodiment, the model 160 may be generated and based on an initially monitored period of neural activity, and then may be adjusted gradually as more and more neural activity is monitored. Thus, the model 160 may be generated over a duration, where the model 160 may be incrementally adjusted during the duration as more neural activity is monitored and more data is available from which to fine tune the model 160.

A desired instance to stimulate may be determined based on the motor movement command. For example, it may be desired to stimulate during and/or immediately after a motor movement command is generated in the motor cortex. Thus, the delivery timing of the stimulation may be determined relative to when the motor movement command is generated by the motor cortex. In the example of locomotion, the motor cortex may generate a motor movement command to step up, immediately before foot off. The motor cortex activity associated with the motor movement command to step up may be learned by monitoring motor cortex activity during attempted stepping. Then, when the motor movement command is generated, the command may be identified based on the learned neural activity pattern that represents the motor movement command to step. The electrical stimulation may be delivered in coordination with the motor movement command to facilitate the stepping. For example, the electrical stimulation may be delivered during and/or immediately after the brain generated motor movement command to step. In this way, the delivery of the electrical stimulation may be timed to mimic when the brain generated motor movement command would ordinarily be communicated by the spinal cord to the appropriate muscles responsible for executing the command step, absent spinal cord injury.

Thus, when current neural activity approximately matches the neural activity patterns associated with a desired instance to stimulate (e.g., brain generated motor movement command), such that the probability that the desired instance is occurring, then, stimulation may be triggered, and a stimulation command signal 162 may be provided to the stimulator 111. As such, the stimulator 111 may deliver stimulation (e.g., electrical pulse).

Neural activity 164 may again be monitored following application of the stimulation, and a new motor movement command model 170 may be generated based both on the neural activity 158 in the absence of stimulation and on the neural activity 164 monitored during and/or after application of the stimulation by the stimulator 111. In this way, the new motor movement command model 170 may account for the effects of the stimulation delivered by the stimulator 111 on neural activity.

Thus, calibration 174 of the neuroprosthetic system may comprise identifying an expected neural activity pattern for a desired instance to deliver stimulation, while accounting for the effects of the stimulation on neural activity. The expected neural activity pattern may be described mathematically via a neural vector 166. Thus, the neural vector 166 may be described in the updated motor movement command model 170.

Thus after the calibration 174, a comparator 180 may compare current neural activity data 168 to the neural vector 166 associated with neural activity that would be expected when it is desired to deliver stimulation (e.g., during and/or immediately after a brain generated motor movement command).

Thus, when an amount of similarity between the current neural activity data, and the neural vector 166 is greater than a threshold, the comparator 180 may determine that it is desired to stimulate, and may send a stimulation command signal 172 to the stimulator 111 to deliver the stimulation. The stimulation may affect the current neural activity data, similarly to when stimulation was delivered during calibration 174. However, by accounting for the effects of stimulation in the updated motor movement command model 170, the comparator 180 may not trigger stimulation in response to the neural activity resulting from the stimulation.

Figure 1C:
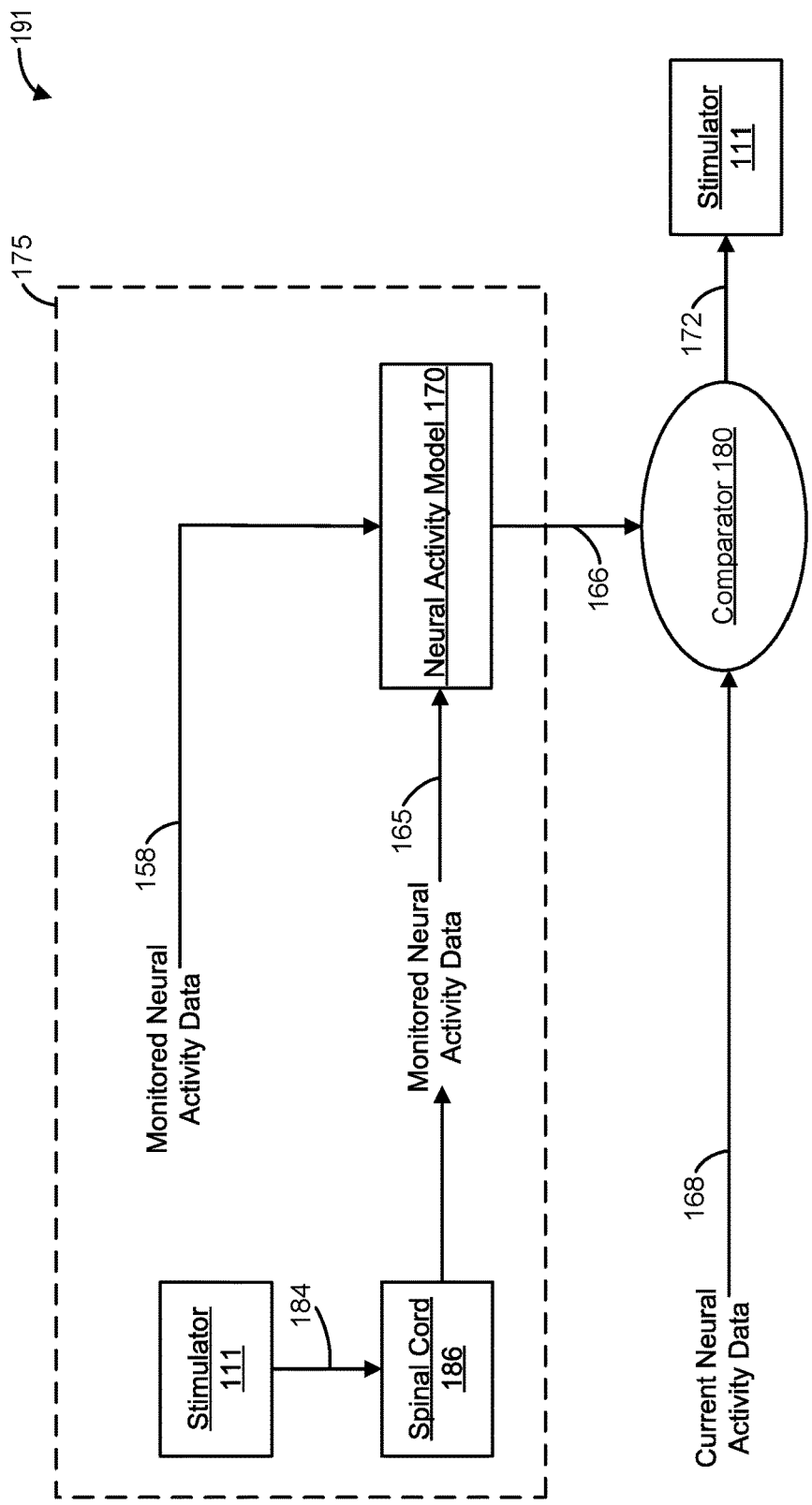
FIG. 1C shows a block diagram of a second example control routine for closed-loop controlling delivery of stimulation of stimulator of a neuroprosthetic system, such as the example neuroprosthetic system of FIG. 1A, in accordance with an embodiment of the present disclosure.

FIG. 1C shows an example schematic 191 of a second control scheme for regulating delivery of stimulation provided by a stimulator of a neuroprosthetic. The schematic 191 of the second control scheme shown in FIG. 1C has similar components as the first control schematic 190 shown in FIG. 1B. As such, similar components in FIG. 1C to those of FIG. 1B are not re-described below for the sake of brevity. Briefly, the stimulation control scheme provided in FIG. 1C may be used in the neuroprosthetic system 100 described above in FIG. 1A, for example. A first set of neural activity data 158 may be monitored after a user is prompted to perform a motor movement via a neurosensor (e.g., neurosensor 112 described above in FIG. 1A). The neural activity data 158 may be collected while the stimulator 111 does not deliver stimulation. As the motor movement is attempted in another instance, a second set of neural activity data 165 may be monitored and stimulation may be triggered at a desired time. In another example, a second set of neural activity data 165 may be monitored and stimulation may be triggered at any instance and/or at random, irrespective of when the user 110 was prompted to perform motor movements, the user's neural activity, or any other sensor data recorded from or around the user 110. Stimulator 111 may deliver electrical stimulation 184 to a spinal cord 186. Thus, brain activity monitored while the stimulator 111 was inactive and stimulation was not delivered to the spinal cord 186, and brain activity monitored while the stimulator 111 was active and stimulation was delivered to the spinal cord 186 may be compiled to create motor movement command model 170. In this way, the motor movement command model 170 may be generated based both on the neural activity 158 in the absence of stimulation and on the neural activity 165 monitored during and/or after application of the stimulation by the stimulator 111. In contrast to the control scheme shown in FIG. 1B for calibration 174, the motor movement command models with and without stimulation generated in calibration 175 may not be sequential phases. That is, motor movement command model 160 may be inputted for motor movement command model 170 but motor movement command model 160 need not temporally proceed monitoring neural activity during stimulation which is also used to generate the new neural activity 170. That is, a single motor movement command model may be generated after brain activity has been monitored both in the presence and absence of stimulation. However, the motor movement command model 170 may be indicative of neural activity representing a brain generated motor movement command. As such, the motor movement command model 170 may be identified by monitoring the neural activity recorded while execution of the motor movement is attempted.

Thus after the calibration 175, a comparator 180 may compare current neural activity data 168 to the neural vector 166 associated with neural activity that would be expected when it is desired to deliver stimulation. Comparator 180 may also be referred to herein as decoder 180. Thus, the comparator 180 may be a decoder, which performs one or more mathematical transformations, operations, filters, regressions, etc., to the processed neural activity signal that is indicative of the raw neural activity monitored/recorded via the neurosensor. For example, the decoder 180 may execute the model 170.

Figure 3:
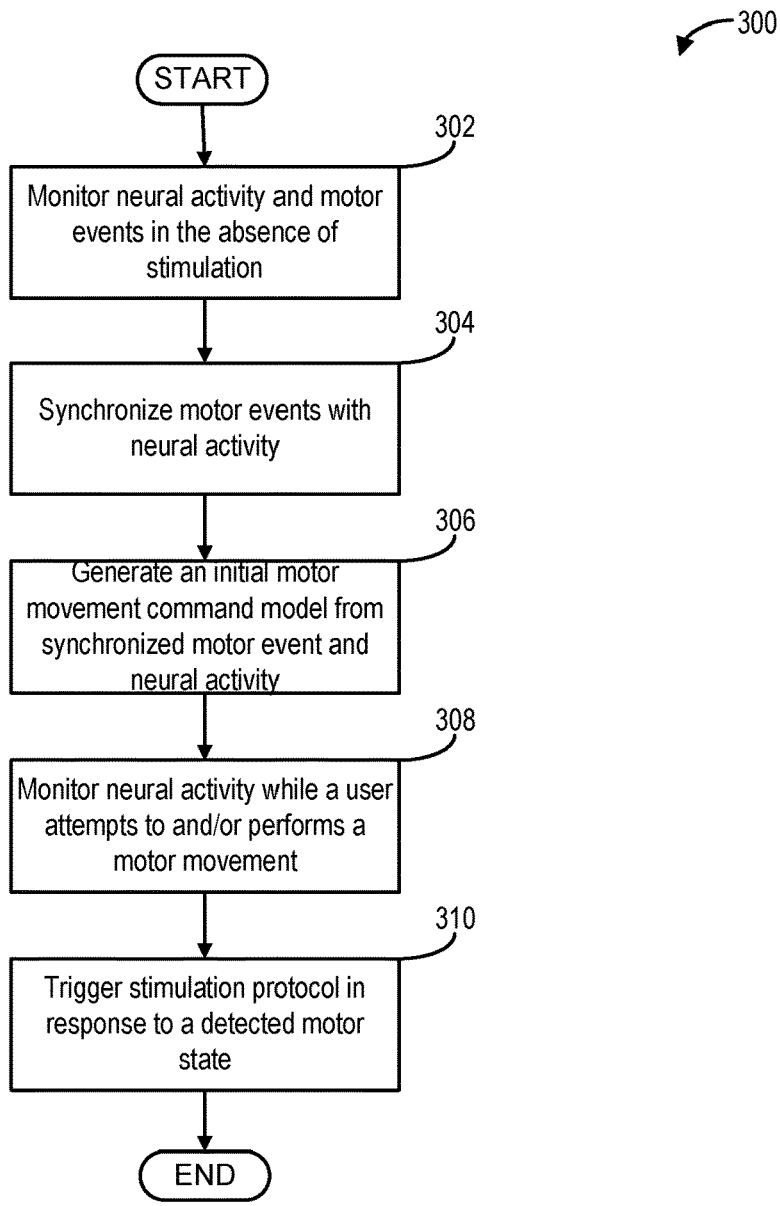
FIG. 3 shows a flow chart of an example method for identifying a neural activity pattern associated with a desired instance to deliver electrical stimulation to a central nervous system via a stimulator of a neuroprosthetic system, such as the example neuroprosthetic system of FIG. 1A, in accordance with an embodiment of the present disclosure.

Thus, the model 170 may comprise one or more calculations to be performed on the neural activity data. For example, the model 170 may be described in greater detail below with reference to FIG. 3. The model 170 for example, may comprise mathematical operations, for when performed, to calculate a likelihood that a motor movement command is being generated in the motor cortex based on the neural activity data. The model 170 is calibrated based on neural activity data monitored during both the presence and absence of stimulation while the motor movement is attempted and/or executed. As such, the decoder 180 may comprise hardware configured to run and execute the model 170. Thus, the decoder 180, may act on the model 170, to determine the likelihood that received neural activity data indicates that a motor cortex generated motor movement command is being generated. FIGS. 3 and 4 show examples of how the model 170 may be calibrated.

Thus, the neural vector 166 may also be referred to more simply as a set point, to which current neural activity data may be compared to determine whether or not to deliver stimulation via the stimulator 111. In some examples, the comparator 180 may determine a similarity between the current neural activity data and the neural vector 166. Thus, when the similarity of current neural activity data, and the neural vector 166 is above a threshold, the comparator 180 may determine that it is desired to stimulate, and may send a stimulation command signal 172 to the stimulator 111 to deliver the stimulation. However, in other examples, the comparator 180 may determine a difference between the current neural activity data and the neural vector 166. Thus, when the difference between the current neural activity data and the neural vector 166 decreases below a threshold, the comparator 180 may determine that it is desired to stimulate.

The stimulation may affect the current neural activity data, similarly to when stimulation was delivered during calibration 174. However, by accounting for the effects of stimulation in the updated motor movement command model 170, the comparator 180 may not trigger stimulation in response to the neural activity resulting from the stimulation.

Figure 2:
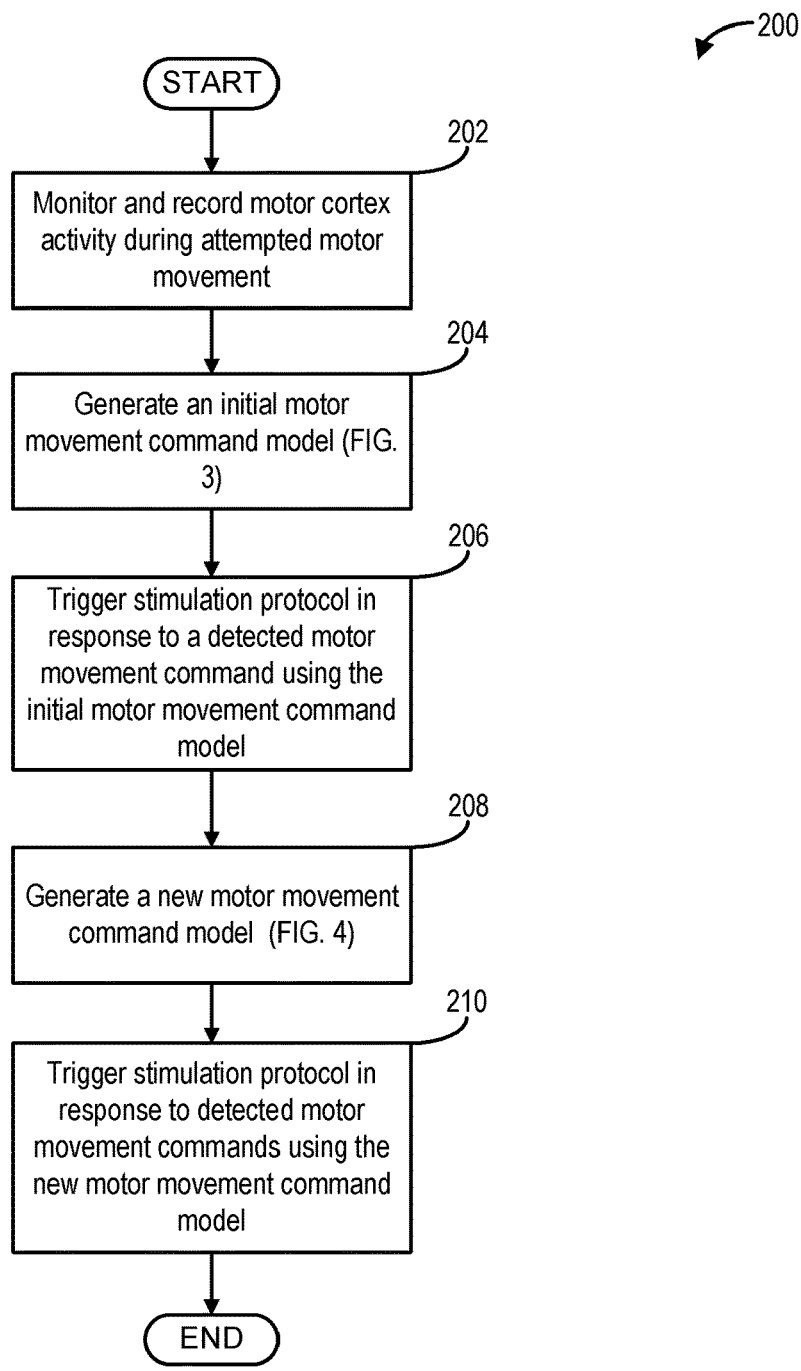
FIG. 2 shows a flow chart of an example method for determining when to deliver stimulation to a central nervous system via a stimulator of a neuroprosthetic system, such as the example neuroprosthetic system of FIG. 1A, in accordance with an embodiment of the present disclosure.

Turning now to FIGS. 2-4, they show example methods for scheduling delivery of stimulation by a stimulator (e.g., stimulator 111 described above in FIGS. 1A, 1B, and 1C) of a neuroprosthetic system (e.g., neuroprosthetic system 100 described above in FIG. 1A). In particular, the neuroprosthetic system may first be calibrated prior to usage in therapy (e.g., motor movement recovery). During calibration, motor cortex activity may be monitored via output from a neurosensor during repeated attempts to perform a desired motor movement or motor event (e.g., stepping). Electrical stimulation may be delivered to the spinal cord at a desired instance. For example, the desired instance to stimulate may be during and/or immediately following generation of a motor movement command signal. The motor movement command signal may be generated by the motor cortex and may command for execution of the desired motor movement. Thus, the desired instance to stimulate is determined based on neural activity monitored while execution of the desired motor movement is attempted. As such, the desired instance to stimulate may be determined relative to when the motor movement command is generated in the motor cortex. As described above with reference to FIGS. 1B-1C, the motor movement command may be identified during attempted execution of the desired motor movement in the absence of stimulation based on monitored motor cortex activity. Thus, the motor movement command may be identified based on the neural activity monitored while execution of the motor movement is attempted. The motor movement command may therefore comprise a distinct neural activity pattern. During calibration therefore, motor cortex activity is monitored and recorded during and after delivery of the electrical stimulation.

After calibration, execution of the motor movement is induced and/or assisted while the motor movement is attempted. Execution of the motor movement may be induced and/or assisted via one or more assisting devices such as a harness, treadmill, etc., and electrical stimulation is delivered to promote movement recovery. The delivery timing of the electrical stimulation may be determined by comparing current neural activity to the model generated during the calibration, where the model is generated based on neural activity monitored during attempted motor movement execution in the presence and absence of spinal cord stimulation. In particular, electrical stimulation may be delivered when the current brain activity approximately matches the brain activity associated with the desired instance to stimulate. By monitoring neural activity during attempted execution of the motor movement while stimulation is delivered, a more accurate model of motor movement commands may be determined.

The methods described below in FIGS. 2-4 may be stored as computer executable instructions and may be stored in non-transitory memory of a controller (e.g., controller 150 described above in FIG. 1A). In particular, the controller may receive an indication of neural activity from a neurosensor (e.g., neurosensor 112 described above in FIG. 1A), and may determine when to trigger stimulation via the stimulator based on the received neural activity data. FIGS. 3 and 4 provide example approaches for calibrating the neuroprosthetic system, and FIG. 2, provides an example approach for delivering stimulation via the stimulator based on the calibration routines described in FIGS. 3 and 4.

Turning to FIG. 2, it shows an example method 200 for determining when to deliver sensory stimulation via the stimulator. In particular, the method 200 may comprise generating a motor movement command model used to trigger electrical stimulation of the spinal cord based on neural response signals with and without stimulation. Calibrating the motor movement command model may include generating a motor movement command model during a motor task using algorithms (such as an algorithm 153 shown in FIG. 1A) and electrically stimulating the spinal cord using a stimulation device (such as stimulation device 111 shown in FIG. 1A). Instructions for carrying out method 200 and the rest of the methods included herein may be executed by a controller (such as controller 150 shown in FIG. 1A) based on instructions stored on a memory of the controller and in conjunction with signals received from one or more sensors of the neuroprosthetic system, such as the sensors described above with reference to FIG. 1A. The controller may employ actuators of the neuroprosthetic system to adjust electrical stimulation of the spinal cord, according to the methods described below. In one example, electrical stimulation to the spinal cord may be supplied by an implantable pulse generator (such as stimulator 111 described above in FIG. 1A).

The method 200 begins at 202 which comprises monitoring and recording motor cortex activity during attempted motor movement. In some examples, the method 200 at 202 may additionally or alternatively comprise receiving motor event data. As described above with reference to FIG. 1A, the motor event data may comprise a visual or spatial representation of user movement and/or orientation. At 202, the method includes receiving signals from a neurosensor (such as neurosensor 112 shown in FIG. 1A) that records motor cortex activity during kinematic activity in the absence of spinal cord stimulation. Additionally, receiving neural activity recordings from a neurosensor may include bandpass filtering and thresholding to identify neural spike events or other neural activity correlates. Further, the method at 202 includes receiving kinematic (e.g. gait) event data from one or more of a video recording and an electromyogram of kinematic activity. In one example, motion capture information (such as motion capture system 120 shown in FIG. 1A) for a user is relayed to the controller. In another example, muscle electrical activity output from an electromyogram (such as electromyogram 130 shown in FIG. 1A) for a user are relayed to the controller. Receiving motor cortex activity and kinematic information includes monitoring neural activity and kinematic data for multiple iterations of a motor task during unstimulated conditions. In one example, motor cortex activity and kinematic data may be recording over multiple gait cycles on a treadmill (such as treadmill 145 shown in FIG. 1A) or during over ground walking with or without walking assistance.

The method continues from 202 to 204 which includes generating an initial motor movement command model. However, in some examples, the method 200 may proceed directly from 202 to 206, and the initial model may not be generated. Thus, in some examples, only the new model may be generated during calibration. In response to the controller receiving neural activity and kinematic recordings, the controller creates a profile of neural activity during movement without stimulation, as described further below with regard to FIG. 3. In particular, the method 200 at 204 may comprise generating a set of neural vectors that mathematically describe an identified neural activity patterns that are associated with a desired instance to deliver stimulation and not deliver stimulation, as well as a matrix that will constrain the space of neural activity to a subspace relevant for detection of those motor movements. The desired instance to deliver stimulation may be during or immediately after a motor cortex generated command signal commanding for execution of the desired motor movement.

In another example, the desired instance to deliver stimulation may be delayed with respect to the motor cortex generated command signal commanding for execution of the desired motor movement in order to specifically facilitate later portions of that movement. Thus, the desired instance may be after the brain generated motor movement command signal. As such, the stimulation may be delivered after the brain generated command signal is generated in the motor cortex to mimic when the signal would ordinarily pass through the spinal cord at the location of electrical stimulation, absent spinal cord injury.

In yet another example, where the movements are cyclical (e.g. locomotion), the motor cortex generated command signal commanding for execution of specific portion of the motor movement (e.g. lifting the right foot) may be used to deliver stimulation throughout the whole or portions of the movement cycle by incorporating one or more delays for one or more stimulation protocols. In such examples, each stimulation protocol may promote one or more portions of the cyclic movement.

In yet another example, the motor cortex generated command signal commanding for execution of a complex movement (e.g. hand reach and grasp or stand up) may be used to deliver stimulation throughout the whole or portions of the complex movement. In such examples, stimulation may be delivered during or immediately after the motor cortex generated command signal commanding for execution of a complex movement and may then continue by incorporating one or more delays for one or more additional stimulation protocols.

In yet another example, the motor cortex generated command signal commanding for execution of a motor movement may be used to terminate otherwise ongoing stimulation immediately or with a set delay. More generally, several otherwise ongoing stimulation protocols may be terminated, each immediately or with its own set delay, at the motor cortex generated command signal commanding for execution of a motor movement.

Next, at 206, the method includes triggering a stimulation protocol in response to a detected motor movement command using the initial motor movement command model. In particular, the method 200 at 206 may comprise monitoring current neural activity and determining when the motor cortex is generating and/or has generated a motor movement command. The motor movement command may be detected by comparing the current neural activity to the initial motor movement command model. More specifically, the method 200 comprises determining an amount of similarity between current neural activity and the initial motor movement model, and detecting a motor movement command when the similarity between the current neural activity and the initial motor movement command model increases above a threshold. The method may comprise delivering the electrical stimulation in response to detecting the motor cortex generated motor movement command, or may delay the electrical simulation according to one or more pre-set delays as described above at 204. Thus, the electrical simulation is delivered at the desired instance in response to the detection of the motor cortex generated motor movement command.

During attempted motor movement execution, the neural activity pattern that represents the motor movement command may be learned and/or identified. Current brain activity may be compared to the motor movement command model, the motor movement command model generated based on brain activity patterns representing the motor movement command, and stimulation may be triggered at the desired instance, where the desired instance may be at, or immediately after when the motor movement command is generated. Triggering stimulation of the spinal cord may include relaying a stimulation protocol to a stimulation programmer (such as stimulation programmer 114 shown in FIG. 1A) and electrically stimulating the spinal cord with a stimulation device (such as implantable pulse generator 111 shown in FIG. 1A). At 208, the method includes generating a new motor movement command model. During a second mode, the controller updates the initial motor movement command model to adjust for the effects of stimulation on neural activity during kinematic activity, as described further below with regard to FIG. 4. In some examples, the method 200 at 208 may modify the neural vector generated at 204 based on the neural activity resulting from the stimulation. In other examples, the method 200 at 208 may comprise leaning a neural response signal associated with the neural activity resulting both in the absence of stimulation and from delivery of the stimulation. Calibration of the neuroprosthetic system may be complete after 208 is executed. Thus, once 208 is executed, the neuroprosthetic may be calibrated and may be ready for motor movement recovery therapy.

After generating the new motor movement command model, method 200 proceeds from 208 to 210 which includes triggering the stimulation protocol in response to neural activity based on the new motor movement command model. The stimulation may be triggered in response to detection of a motor cortex generated motor movement command in the same or similar manner to that described above at 206, except that in 210, the motor movement generation is detected based on the new model which accounts the effects of stimulation on neural activity.

Specifically, in response to the controller receiving neural activity and kinematic recordings, stimulation is delivered to the spinal cord by a stimulation device (such as stimulation device 111 shown in FIG. 1) based on the motor movement command model. In one example, where the neuroprosthetic system is used to alleviate lower limb motor deficits, the stimulation may be delivered over different spinal segments ranging from L1 to S5. In another example, flexion movements of the left and right leg may be promoted by stimulating 0.5 mm left and right at spinal segment L2, respectively. However, in other examples, the stimulation may delivered more or less than 0.5 mm left and right at spinal segment L2. In yet another example, flexion movements of the left and right leg may be promoted by stimulating 0.5 mm left and right at spinal segment L2, respectively, by initiating stimulation at these locations preceding the foot off event by 100 ms and lasting for 300 ms. However, in other examples, the stimulation may delivered more or less than 0.5 mm left and right at spinal segment L2, may be delivered more or less than 100 ms preceding the foot off event, and may be delivered for more or less than 300 ms.

In yet another example, extension movements of the left and right leg may be promoted by stimulating 0.5 mm left and right at spinal segment L2, respectively. However, in other examples, the stimulation may delivered more or less than 0.5 mm left and right at spinal segment L2. In yet another example, extension movements of the left and right leg may be promoted by stimulating 0.5 mm left and right at spinal segment L2, respectively, by initiating stimulation at these locations preceding the foot off event by 100 ms and lasting for 400 ms. However, in other examples, the stimulation may delivered more or less than 0.5 mm left and right at spinal segment L2, may be delivered more or less than 100 ms preceding the foot off event, and may be delivered for more or less than 400 ms.

In yet another example, where the neuroprosthetic system is used to alleviate upper limb movement deficits, the stimulation may be delivered over different spinal segments ranging from C3 to T1. The stimulation protocol delivered at 210 is based on a method similar to the method at 310 of FIG. 3. However, at 210, the method includes adding neural activity observed with stimulation to the neural vector and triggering stimulation using the new motor movement command model as described further below with regard to FIG. 4. Further, the method 200 at 210 may comprise assisting and/or inducing execution of the motor movement via one or more assisting devices such as a treadmill, harness, etc.

In some examples, where the method proceeds directly from 202 to 206 and does not generate the initial motor movement command model, neural activity is monitored during attempted execution of the motor movement during the calibration. Stimulation may be delivered at the desired instance at 206, and then the motor cortex activity monitored and recorded during and after the stimulation may be used in conjunction with the brain activity monitored and recorded prior to the delivery of the stimulation to generate the new motor movement command model. That is, during calibration, stimulation may be delivered at the desired instance, and motor cortex activity may be monitored and recorded during attempted execution of the motor movement. After calibration, brain activity is then compared to the motor movement command model. When current brain activity substantially matches the brain activity at the desired instance determined during calibration, such that the likelihood that the desired instance is occurring is sufficiently high (e.g., greater than a threshold), stimulation may be delivered. Specifically, current motor cortex activity is compared to the new motor movement command model to detect when a motor cortex generated motor movement command is generated in the motor cortex. A motor cortex generated motor movement command may be detected when current neural activity approximately matches the new motor movement command model (e.g., similarity between current neural activity and the new motor movement command model increases above a threshold). Thus, while motor cortex activity is being monitored, the motor movement command model is used to determine a likelihood that the motor movement command is being generated.

In this way, the motor movement command model used to trigger stimulation of the spinal cord may be calibrated, such that the spinal cord is stimulated at the appropriate times during locomotion and stimulation effects are accounted for. Said another way, by calibrating a model using both the data in absence and in presence of effects of the stimulation on the monitored neural activity, undesirable stimulations may be avoided and desirable stimulation may be delivered at the appropriate times.

FIG. 3 shows an example method 300 for generating an initial motor movement command model during kinematic activity. The method 300 continues from the method at 202 of FIG. 2 in response to receiving motor and neural activity information for a user performing a motor task without stimulation. In particular, method 300 may be executed during a first phase of a calibration of a neuroprosthetic. The method 300 may be executed to calibrate the neuroprosthetic and to determine a desired instance to deliver stimulation. Specifically, the method 300 may be executed to identify and/or learn a motor movement command generated by the motor cortex that commands for execution of the desired motor movement (e.g., stepping). By monitoring motor cortex activity while the desired motor movement is attempted, the motor movement command for the desired motor movement may be learned. In some examples, the method 300 may be executed to generate an initial motor movement command model that identifies instances when it is desired to deliver electrical stimulation from on the motor cortex activity that would be expected at those instances (e.g., during and/or immediately after generation of the motor movement command).

The method 300 begins at 302 by monitoring neural activity (e.g., motor cortex activity) and motor events in the absence of stimulation. Motor events may be identified from kinematic recordings (e.g. motion capture system 120 shown in FIG. 1A), kinetic recordings (e.g. muscle activity from an electromyogram 130 shown in FIG. 1A), or any other sensor that records behavior (e.g. accelerometers, force plates, etc.). The motor events may comprise any one or more specific events included and/or executed during the course of a more complex coordinated motor movement, such as a foot off event during the gait cycle of locomotion, and/or the motor events may comprise one or more complex, coordinated movements such as reaching and/or retracting of an arm, stepping, walking, grasping, etc.

As described above, motor cortex activity and kinematic event data during repeated cycles of a motor task (e.g., locomotion) is relayed to the controller. The controller receives neural activity recordings, as well as kinematic event data, during a motor task that is repeated for two or more cycles. Neural activity recordings may include motor cortex activity information from a neurosensor (such as neurosensor 112 shown in FIG. 1A). Neural activity signals may be analyzed by the controller to identify neural spike events. Then, at 304, the method includes coordinating motor events with neural spike events. Neural spike events that are identified from motor cortex activity during the motor task are aligned with a motor events during movement for each of the cycles recorded. For example, neural spike events during locomotion may be aligned with specific motor events during locomotion, such as foot strike and foot off. Next, the method at 306 includes generating an initial motor movement command model based on neural activity during the motor movement. The initial motor movement command model is then generated by creating a set of mean motor cortex activities, each over repeated cycles of the kinetic event, a mean of motor cortex activities over all other epochs (epoch during which not to use to initiate stimulation), and a matrix that will project the monitored neural activity into a subspace relevant for identification of motor events. In this way, the model identifying motor commands, which are concurrent or precede motor events used to calibrate the model, from the motor cortex activity may be created.

In particular, generating the initial motor movement command model may comprise generating one or more neural vectors describing the average neural activity patterns that occur at a desired instance during execution of the motor movement at which delivering stimulation is desired, generating a neural vector describing the average neural activity pattern that occurs at a desired instance during execution of the motor movement at which stimulation is not desirable, and generating a matrix that will project the monitored neural activity into a subspace relevant for identification of motor events. For example, it may be desired to deliver stimulation at pre-set instances during execution of the motor movement. By time-aligning (e.g., synchronizing) the neural activity data with the kinematic events recorded during execution of the motor movement, the average neural activity patterns during, immediately preceding, and/or at the pre-set instances may be determined and described via the neural vector. For example, let the set of motor movements at which it is desirable to initiate stimulation be composed of four different events: right foot off (rfo), left foot off (lfo), right foot strike (rfs) and left foot strike (lfs). After recording the neural activity and kinematics over a period of time and synchronizing the two, let RFO, RFS, LFO and LFS be the sets containing the times when the rfo, rfs, lfo and lfs events occurred. For example, the neural activity may be recorded using a neurosensor consisting of $N_{ch}$ channels. In another example, we may compose neural vectors at time t, a(t), by collecting neural recordings at each channel at time t, t—$\Delta$t and t–2$\Delta$t. Calibration composes generating sets of neural vectors a(t) collected at time rfs(i), rfo(i), lfs(i) and lfo(i), termed $C_{RFO}$, $C_{RFS}$, $C_{LFS}$, $C_{LFO}$, where i stands for the i-th occurrence of that motor movement.

$$C_{RFO} = \left\{ \bar{a}_{RFO} \mid \bar{a}_{RFO}(i) = \begin{bmatrix} x_1(rfo(i)) \\ x_1(rfo(i) - \Delta t) \\ x_1(rfo(i) - 2\Delta t) \\ x_2(rfo(i)) \\ \vdots \\ x_{N_{CH}}(rfo(i) - 2\Delta t) \end{bmatrix} \right\}$$

-continued $$C_{RFS} = \left\{ \bar{a}_{RFS} \mid \bar{a}_{RFS}(i) = \begin{bmatrix} x_1(rfs(i)) \\ x_1(rfs(i) - \Delta t) \\ x_1(rfs(i) - 2\Delta t) \\ x_2(rfs(i)) \\ \vdots \\ x_{N_{CH}}(rfs(i) - 2\Delta t) \end{bmatrix} \right\}$$

$$C_{LFO} = \left\{ \bar{a}_{LFO} \mid \bar{a}_{LFO}(i) = \begin{bmatrix} x_1(lfo(i)) \\ x_1(lfo(i) - \Delta t) \\ x_1(lfo(i) - 2\Delta t) \\ x_2(lfo(i)) \\ \vdots \\ x_{N_{CH}}(lfo(i) - 2\Delta t) \end{bmatrix} \right\}$$

$$C_{LFS} = \left\{ \bar{a}_{LFS} \mid \bar{a}_{LFS}(i) = \begin{bmatrix} x_1(lfs(i)) \\ x_1(lfs(i) - \Delta t) \\ x_1(lfs(i) - 2\Delta t) \\ x_2(lfs(i)) \\ \vdots \\ x_{N_{CH}}(lfs(i) - 2\Delta t) \end{bmatrix} \right\}$$

In addition, calibration composes generating a set of neural vectors a(t) collected at all times that are at least dt away from any rfs, rfo, lfs and lfo, termed $C_{OTHER}$, $$C_{OTHER} = \left\{ \bar{a}_O \mid \bar{a}_O(i) = \begin{bmatrix} x_1(t_i) \\ x_1(t_i - \Delta t) \\ x_1(t_i - 2\Delta t) \\ x_2(t_i) \\ \vdots \\ x_{N_{CH}}(t_i - 2\Delta t) \end{bmatrix}, \begin{array}{l} t_i < rfo - 10 \text{ ms} \\ t_i > rfo + 10 \text{ ms} \\ t_i < rfs - 10 \text{ ms} \\ t_i > rfs + 10 \text{ ms} \\ t_i < lfo - 10 \text{ ms} \\ t_i > lfo + 10 \text{ ms} \\ t_i < lfs - 10 \text{ ms} \\ t_i > lfs + 10 \text{ ms} \end{array} \begin{array}{l} \forall rfo \in RFO \\ \forall rfs \in RFS \\ \forall lfo \in LFO \\ \forall lfs \in LFS \end{array} \right\}$$

Calibration may compose a random, algorithmic, or heuristic way of selecting which of the times other than any rfs, rfo, lfs and lfo to include for generation of the $C_{OTHER}$ set. Furthermore, calibration may comprise calculating means of all neural vectors in the $C_{RFO}$, $C_{RFS}$, $C_{LFS}$, $C_{LFO}$ and $C_{OTHER}$ sets, $m_{RFO}$, $m_{RFS}$, $m_{LFS}$, $m_{LFO}$ and $m_{OTHER}$. In addition, calibration may comprise calculating a covariance matrix CC of all the neural vectors a(t) that belong to a set CALL composed of all members of $C_{RFO}$, $C_{RFS}$, $C_{LFS}$, $C_{LFO}$ and $C_{OTHER}$ sets that have been had $m_{RFO}$, $m_{RFS}$, $m_{LFS}$, $m_{LFO}$ and $m_{OTHER}$ subtracted from them, respectively. Furthermore, calibration may compose of calculating a regularized covariance matrix CC* from the covariance matrix CC, a parameter g, mean of diagonal entries of covariance matrix CC and a unit matrix I.

$$CC^* = (1-g)CC + g \cdot \text{mean}(\text{diag}(CC)) \cdot I$$

Thus, by monitoring the neural activity over multiple repetitions of the movement, and synchronizing the neural activity data with the kinematic activity data, a desired instance during execution of the motor movement during which it is desired to deliver the stimulation may be predicted based on the neural activity data.

After creating the initial motor movement command model, the method 300 may continue from 306 at 308 which includes monitoring motor activity during kinematic activity. Then, at 310, the method includes triggering a stimulation protocol in response to a detected motor activity. At 310, the initial motor movement command model is used to determine the desired timing during the cycle of the motor event to trigger stimulation. In particular, the method 300 at 310 may comprise one or more of band-pass filtering the neural activity data, identifying spike event by thresholding the neural activity data, estimating spike rates at regular intervals (e.g., 10 ms) by summing up all of the spikes over a previous first duration (e.g., 150 ms), extracting neural features by selecting a number of equidistantly sampled spike rates preceeding the motor events over a selected period (e.g., 500 ms), and creating current neural vectors by concatenating a selected number of neural features. The motor movement command generated at 306 may then act on the current neural vector to determine the likelihood that the desired instance to stimulate is occurring. For example, the probability, $p_{event}(t)$, that the desired instance to stimulate in response to the event is occurring based on the current neural vector, $v(t)$, may be described according to the equation 1 below:

$$p_{event}(t)=\exp(-(v(t)-m_{event})*CC^{-1}(v(t)-m_{event})^T) \quad [1]$$

In equation 1, $m_{event}$ represents the neural vector generated at 306. Further, CC in equation 1 represents the shared neural vector covariance matrix or the regularized shared neural vector covariance matrix generated at 306. Then, the likelihood that the desired instance is occurring may be determined according to equation 2 below:

$$p_{event}'(t)=p_{event}(t)/(\Sigma_{i=1}^{number\ of\ motor\ events}p_i(t)+p_{no\ event}(t)) \quad [2]$$

In equation 2, $p_{event}'(t)$ represents the likelihood that the desired instance during which it may be desired to stimulate is occurring. The $p_{no\ event}(t)$ term represent the probability that the desired instance is not occurring which may be calculated in a similar manner to $p(t)$, according to equation 3:

$$p_{no\ event}(t)=\exp(-(v(t)-m_{no\ event})*CC^{-1}(v(t)-m_{no\ event})^T) \quad [3]$$

Then, the likelihood that the desired instance is not occurring may be determined according to equation 4 below:

$$p_{no\ event}'(t)=p_{no\ event}(t)/(\Sigma_{i=1}^{number\ of\ motor\ events}p_i(t)+p_{no\ event}(t)) \quad [4]$$

In equation 3, the $m_{no\ event}$ represents the mean neural vectors excluding the desired event, or the mean neural vectors that do not include the neural vectors associated with the desired instance to stimulate. It should be appreciated that the above equations can easily be manipulated to include the probabilities of additional events in examples where there is more than one desired instance to provide stimulation during execution of the motor movement.

At 310, it is important to trigger the stimulation in such a way not to have the initial motor movement command model detecting motor events while the neural activity is affected by the stimulation. For example, if the effect on the neural activity persists during the stimulation and following the stimulation by $T_f$ time, and if the stimulation duration is $T_D$, than the method may include a heuristic that another motor event may not be identified based on the monitored neural activity $T_f+T_D+T_S$ after an event has been identified, where $T_S$ is a temporal offset included to allow some safety margin. In this way, the initial motor movement command model may always work in its assumed regime, i.e. while the monitored neural activity is not affected by stimulation. At 310, the method may include triggering the stimulation in response to only one type of motor event for which the model has been calibrated. If the subjects behavior is such as to prevent two motor events of the same type to occur more frequent than every $T_f+T_D+T_S$ for that movement event, the initial model may again always work in its assumed regime. This may be achieved by calibrating a single model designed to predict all types of motor movements that are intended to be followed by stimulation and implementing a heuristic that permits stimulation only after a single selected motor movement has been detected. This may also be achieved by calibrating more than one model, each of which may be designed to detect one or more motor movements. In this way, the employed motor movement command model detects desired motor movements from the monitored neural data only when the stimulation effect on the neural data has worn off.

Figure 4A:
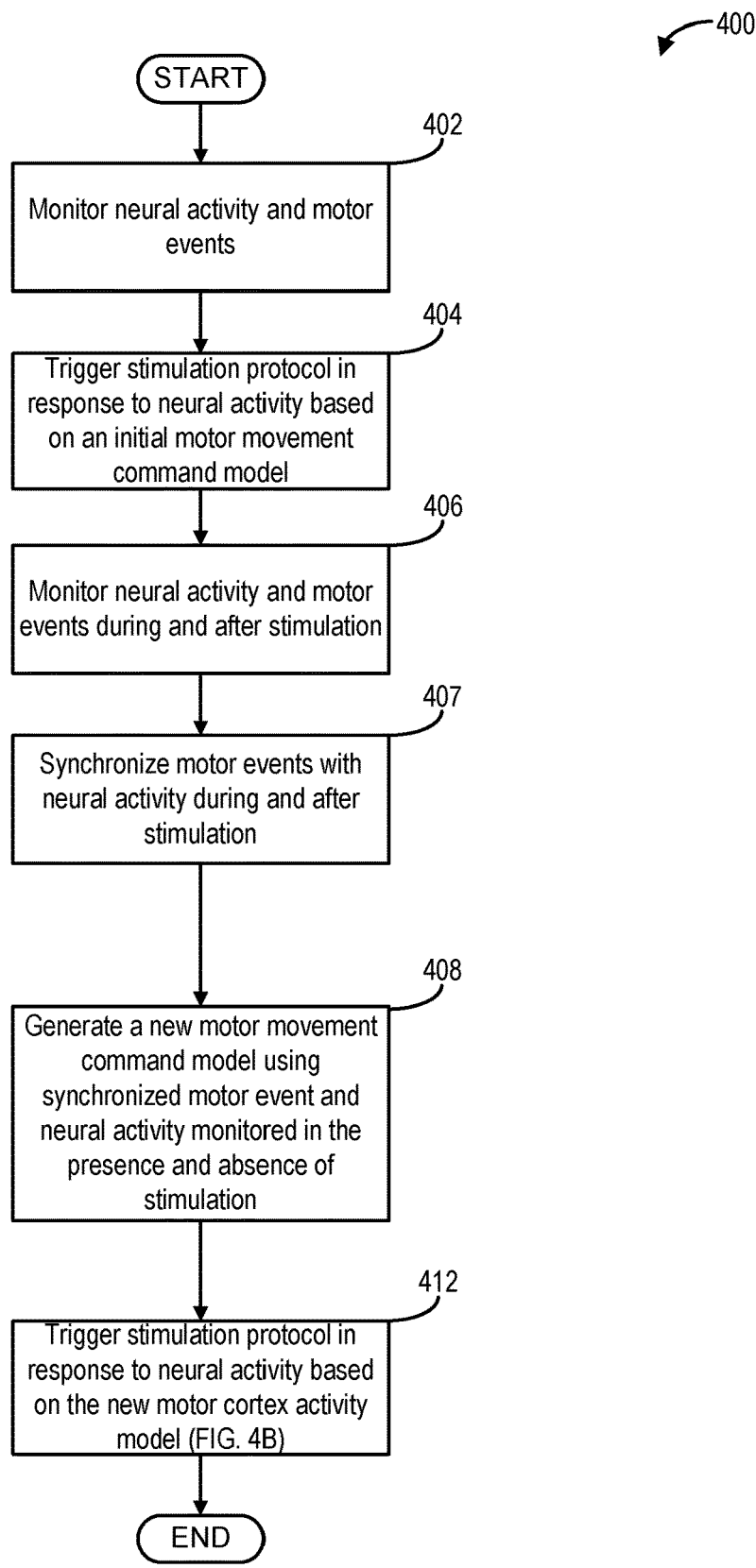
FIG. 4A shows a flow chart of an example method for learning a neural response signal generated due to stimulation of the central nervous system, and adjusting stimulation of the central nervous system via a stimulator of a neuroprosthetic system, such as the example neuroprosthetic system of FIG. 1A, based on the learned neural response signal, in accordance with an embodiment of the present disclosure.
Figure 4B:
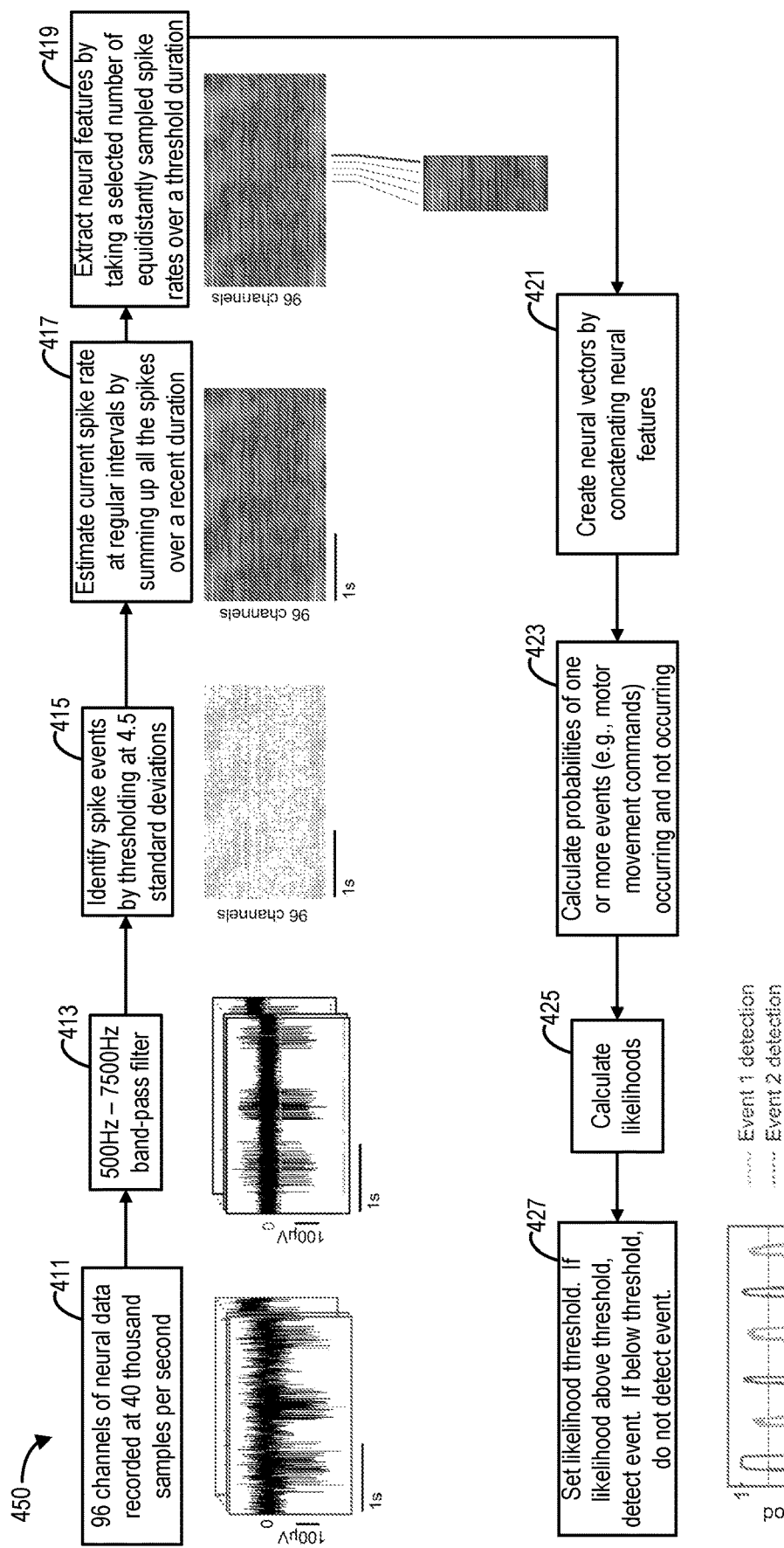
FIG. 4B shows a flow chart of an example method for determining when to deliver stimulation to the central nervous system via a stimulator of a neuroprosthetic system, such as the example neuroprosthetic system of FIG. 1A, based on current neural activity and neural activity monitored during attempted execution of a motor movement, in accordance with an embodiment of the present disclosure.

FIGS. 4A and 4B show flow charts of example methods for determining when to deliver electrical stimulation via the stimulator. In particular, FIG. 4A shows an example method 400 for updating an initial motor movement command model that is used to trigger electrical stimulation of the spinal cord. The method 400 continues from the method at 206 of FIG. 2 in response to triggering stimulation of the spinal cord during a motor task using the initial motor movement command model. For example, method 400 may be executed while a motor movement is attempted. Method 400 may comprise delivering stimulation at a desired instance. FIG. 4B shows an example method 450 for monitoring current neural activity and using a motor movement command model to identify motor events associated with the desired instance to stimulate from the current neural activity. A likelihood that the desired instance is occurring may be determined based on the probability that current neural activity belongs to the set of neural activity patterns representing the desired instance to stimulate that were used to calibrate the model (e.g., when the motor movement command is generated in the motor cortex).

Focusing on FIG. 4A, the method 400 begins at 402 by monitoring neural activity and motor events. The controller receives neural activity recordings, as well as motor events, during a motor task that is repeated for two or more cycles. Motor events may be identified using kinetic activity, which may include one or more of muscle activity recordings from an electromyogram (such as electromyogram 130 shown in FIG. 1A), or kinematic recordings, which may include a video recording of a user performing a motor task from a motion capture system (such as motion capture system 120 shown in FIG. 1A). Neural activity recordings may include motor cortex activity information from a neurosensor (such as neurosensor 112 shown in FIG. 1A). The controller may apply a bandpass filter to neural activity recordings and threshold to identify neuronal spike events.

Next, at 404, the method includes triggering a stimulation protocol in response to neural activity based on the initial motor movement command model in the same or similar manner to that described at 310 of method 300 in FIG. 3. During kinematic activity, neural activity is monitored and the initial motor movement command model is employed to trigger spinal cord stimulation at desired times during the motor task. For example, the controller may receive inputs from a neurosensor (such as neurosensor 112 shown in FIG. 1A) and employ the initial motor movement command model to transmit stimulation commands to a stimulation programmer (such as stimulation programmer 114 shown in FIG. 1A). In response to a command to provide electrical stimulation to the spinal cord, a stimulation device (such as stimulation device 111 shown in FIG. 1A) may be operated to trigger spinal cord stimulation.

At 406, the method includes monitoring neural activity during and after stimulation. As described above, monitoring neural activity may include receiving inputs from a neurosensor (such as neurosensor 112 shown in FIG. 1A) and using a threshold to identify neuronal spike events. Further, the method at 406 includes monitoring motor cortex activity for a duration following stimulation during motor activity in order to capture neural activity throughout the epoch while the stimulation affects the neural activity. The controller may receive neural activity from a neurosensor.

In some examples, the method 400 at 406 may comprise monitoring neural activity for a plurality of repetitions of the motor movement, and thus delivering the stimulation more than once. The stimulation may be delivered at the desired instance during each of the repetitions of the motor movement. Further, the method 400 at 406 may comprise waiting at least a set duration between each stimulation. In some examples, the waiting may comprise monitoring neural activity after each stimulation, and not attempting to detect motor events from neural activity in order to initiate further stimulation before the most recent effects of stimulation on neural activity have terminated. In yet further examples, the waiting may comprise learning a maximum duration that the effects of the stimulation on neural activity persist, and waiting at least that duration after stimulating to enable detection of motor events in order to stimulate again. In this way, different stimulations may be separated by at least the duration of the neural response signal. That is, the controller may not control delivery of the stimulation based on the current neural activity for the duration of the neural response signal to the stimulation.

However, in yet further examples, the duration of the neural response signal may be sufficiently long such that stimulation may again be desired after delivery of a most recent stimulation, whereby the neural response signal still persists. That is, in some examples, the neural response signal of separate stimulations may overlap, due to the interval between stimulations being shorter than the duration of the neural response signal. In such examples, the combined effect of the overlapping neural response signals may be learned. Thus, in the examples provided above, delivery timing of the stimulation during the second phase of the calibration may be determined based on desired motor events that occurred during the execution of the motor movement. That is, stimulation may be desired at specific points during each repetition of the motor movement. Stimulation may be administered during the second phase of the stimulation at the desired points during each repetition of the motor movement, and the new motor movement command model may be generated that takes into account the neural response to the stimulation, such that after calibration the neural activity resulting from the stimulation does not trigger stimulation. Thus, during the period following a first stimulation, where first stimulation alters the neural activity from what it would be absent delivery of the first stimulation, stimulation may not be delivered.

Method 400 then continues from 406 to 407 which comprises synchronizing motor events with neural activity during and after stimulation in a similar manner to that described above at 304 of method 300 in FIG. 3.

Then, at 408, the method includes generating a new motor movement command model based both on the neural activity and motor events monitored in the presence and absence of stimulation.

However, in yet further examples, the duration of the neural response signal may be sufficiently long such that stimulation may again be desired after delivery of a most recent stimulation, whereby the neural response signal still persists. That is, in some examples, the neural response signal of separate stimulations may overlap, due to the interval between stimulations being shorter than the duration of the neural response signal. In such examples, the method 400 may include additional calibration steps, where the stimulation may delivered such that the neural effects from separate simulations overlap. In this way, the combined effect of the overlapping neural responses from different stimulations may be learned.

Next, at 412, the method includes triggering a stimulation protocol in response to neural activity based on the new motor movement command model. At 408, the new motor movement command model is used to determine the desired timing to trigger stimulation. In particular, the method at 408 may comprise one or more of band-pass filtering the neural activity, identifying spike event by thresholding the neural activity, estimating spike rates at regular intervals (e.g., 10 ms) by summing up all of the spikes over a previous first duration (e.g., 150 ms), extracting neural features by taking a selected number of equidistantly sampled spike rates over a previous second duration (e.g., 500 ms), and creating modified neural vectors by concatenating a selected number of neural features. The neural vectors are generated by adding neural activity observed during stimulation to the current neural vectors, as described above with regard to 310 of method 300 of FIG. 3. In this way, the new motor movement command model is used to trigger stimulation at desired times based on the neural activity and motor events observed during calibration both with and without stimulation.

Turning now to FIG. 4B, it shows an example method 450 that may be executed at one or more of 310 in method 300 of FIG. 3, and 410 and/or 412 described above with reference to method 400 of FIG. 4A. Thus, method 450 may proceed from one or more of 308 of method 300 in FIG. 3, and/or 408 of method 400 in FIG. 4A. In particular, method 450 may be executed to determine when to deliver stimulation based on current neural activity. Thus, method 450 may be executed during calibration when it is desired to deliver stimulation and/or after calibration during motor movement recovery therapy where stimulation is desired and execution of the motor movement is assisted and/or induced.

Method 450 begins at 411 which comprises recording a plurality of channels of neural data at a specified rate. In the example of FIG. 4B, the plurality of channels comprises 96 channels. However, more or less than 96 channels may be recorded. The specified rate in the example of FIG. 4B is 30,000 samples per second. However, the specified rate may be more or less than 30,000 samples per second in other examples. Method 450 then continues from 411 to 413 which comprises band-pass filtering the neural data between 500 Hz and 7,500 Hz. However, in other examples, no filters or filters with other frequency windows may be used to process the neural activity. Furthermore, in other examples, other neural processing techniques, including short time Fourier transform, down sampling, up sampling, autoregressive spectral power estimation techniques, etc. may be used to process the neural activity. Then at 415, the method 450 may comprise identifying spike events by thresholding at a selected standard deviation. In the example of FIG. 4B, the threshold may be 3.5 standard deviations. However, in other examples, the threshold may be greater or less than 3.5 standard deviations.

Method 450 then continues from 415 to 417 which comprises estimating the current spike rate at regular intervals by summing up all of the spikes over a recent duration. In some examples, the regular intervals may be every 10 ms and the recent duration may be 150 ms. However, in other examples, the regular intervals may be greater or less than 10 ms and the recent duration may be greater or less than 150 ms. Method 450 may then continue from 417 to 419 which comprises extracting neural features by taking a selected number of equidistantly sampled spike rates over a selected duration. The selected number of equidistantly sampled spike rates may be 5. However, in other examples, the selected number of equidistantly sampled spike rates may be greater or less than 5. In one example, the selected duration may be 500 ms. However, in other examples, the selected duration may be greater or less than 500 ms. The method 450 may then proceed from 419 to 421 which comprises creating neural vectors by concatenating a selected number of neural features in the same or similar manner to that described above at 310 of method 300 in FIG. 3. In one example, the method 450 at 421 may comprise creating neural vectors from five neural features from each of the neural channels. However, in other examples more or less than 5 neural features may be used from selected neural channels to create the neural vectors.

Method 450 may then continue from 421 to 423 which comprise calculating probabilities of one or more motor events (i.e., motor movement commands) occurring and not occurring in the same or similar manner as that described above by equations [1] and [3] in 310 of method 300 in FIG. 3. Method 450 may then continue from 423 to 425 which comprises calculating the likelihoods of the one or more events occurring in the same or similar manner as that described above by equation [2] in 310 of method 300 in FIG. 3. Method 450 may then continue from 425 to 427 which comprises determining if the likelihood calculated in 425 is greater than or less than a threshold. In the example of FIG. 4B, the threshold is set to 0.8. However, in other examples, the likelihood threshold may be greater or less than 0.8. If the likelihood of the event occurring increases above the threshold, then it may be determined that the event is occurring or has occurred (e.g., the motor movement command has been generated by the motor cortex) and stimulation may be delivered by the stimulator. Specifically, the controller may send one or more wireless signals to the stimulator commanding the stimulator to initiate the stimulation protocol. However, if the likelihood did not pass the threshold, i.e. the likelihood maintained a value that was below or above the threshold, then it may be determined that the event does not occur and stimulation protocol is not initiated.

Figure 5:
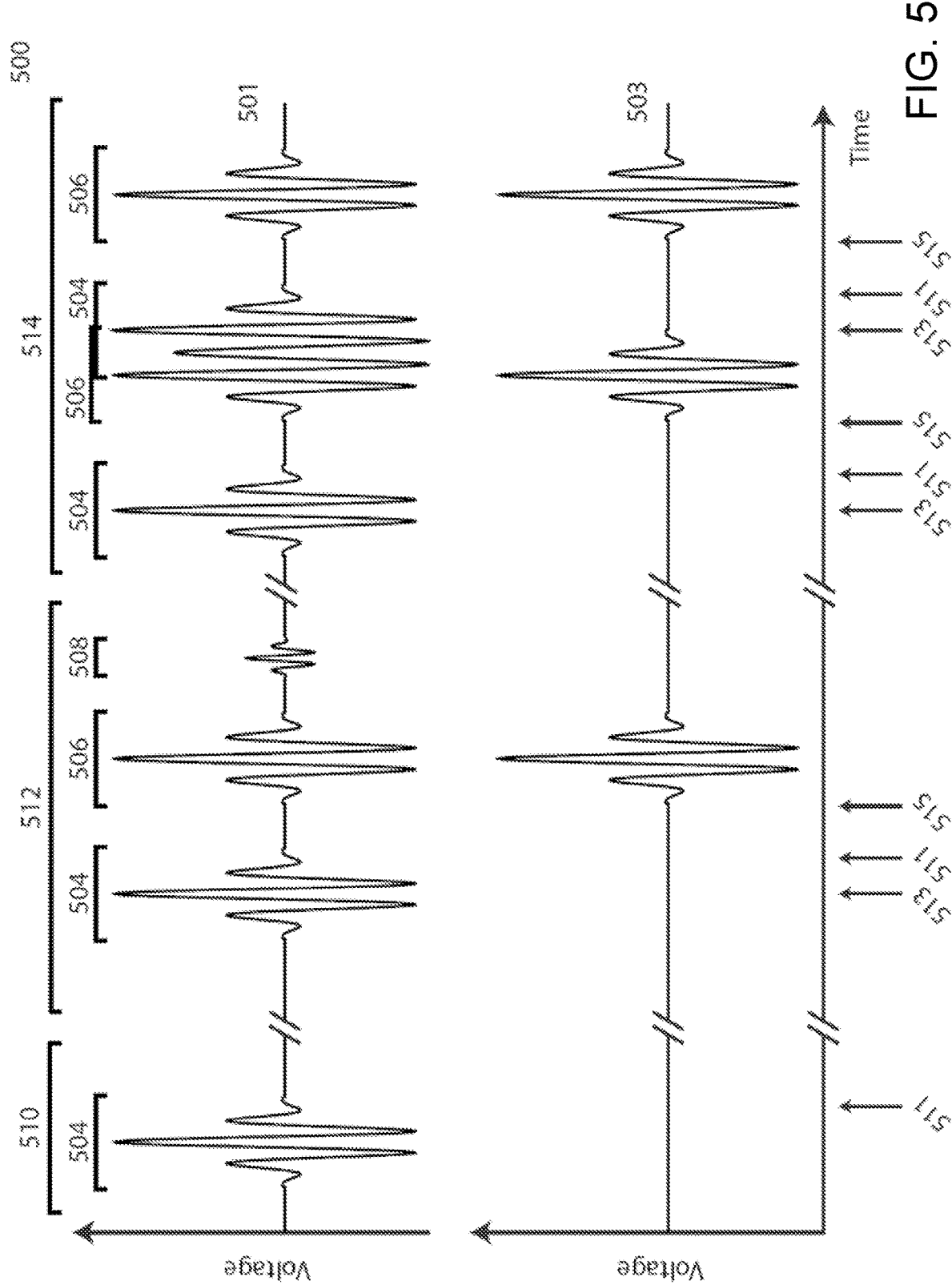
FIG. 5 shows an example graph depicting changes in neural activity resulting from stimulation of the central nervous system via a stimulator of a neuroprosthetic system, such as the example neuroprosthetic system of FIG. 1A, in accordance with an embodiment of the present disclosure.

FIG. 5 shows an example graph 500 depicting changes in neural activity resulting from stimulation of the central nervous system via a stimulator of a neuroprosthetic system, such as the example neuroprosthetic system of FIG. 1A. Specifically, graph 500 shows motor cortex neural activity recorded from two neurosensor channels, respectively shown at plot 501 and plot 503. The neural activity shown in FIG. 5 at plots 501 and 503 may be the output of two neurosensor channels, such as signals recorded on two separate electrodes of a wireless microelectrode array neurosensor (such as neurosensor 112 shown in FIG. 2). As described above, during a first mode, neural response signals are recorded during a motor task and motor cortex neural activity is correlated with motor events in the absence of stimulation at 510. During a second mode at 512, the spinal cord is stimulated using a neuroprosthetic device (such as stimulation device 111 shown in FIG. 1A) and the resulting effect of stimulation on neural activity is monitored. In this way, a neuroprosthetic system is calibrated to account for stimulation effects when triggering spinal cord stimulation to elicit motor behavior. During a third mode, at 514, the neuroprosthetic system, which has been calibrated to account for the stimulation effects, is used to trigger stimulation to elicit motor behavior. In this way, stimulation effects on neural activity are not interpreted as signatures of a desired motor event that the system is using to trigger the stimulation, even though the neural activity that corresponds to the desired motor event and the neural activity in response to the stimulation are identical. Further for graph 500, voltage for neural activity is depicted along the vertical axis and time is depicted along the horizontal axis.

Plots 501 and 503 of FIG. 5 show two example traces of neural activity signals recorded from the motor cortex during a motor activity for three different modes: the first mode, at 510, during which the synchronized motor activity and neural activity is monitored in order to calibrate an initial motor movement command model; the second mode, at 512, during which the initial motor movement command model is used to initiate stimulation and synchronized motor activity and neural activity is monitored in order to calibrate a new motor movement command model; and the third mode, at 514, during which the new motor movement command model is used to initiate stimulation. Additionally, motor events, decoded motor events, and stimulation events are indicated at by vertical arrows and marked as 511, 513, and 515, respectively. Thus, plots 501 and 503 at 510 show two channels of example traces of neural activity recorded from the motor cortex in the absence of electrical stimulation of the spinal cord. Therefore, plots 501 and 503 at 510 show example neural activity that may be observed while monitoring neural activity during a first phase of calibration in which stimulation is not delivered, such as the calibration routine described above in FIG. 3. During 512, plots 501 and 503 show example neural activity that may be observed while monitoring neural activity during a second phase of calibration in which electrical stimulation is delivered, such as the calibration routine described above in FIG. 4. A final motor cortex generated motor command model may be generated based on the neural activity monitored both in the absence (at 510) and presence (at 512) of stimulation. Plots 501 and 503 at 514 shows example neural activity that may be observed while monitoring neural activity after the new motor movement command model has been calibrated in which electrical stimulation is delivered using the new motor movement command model.

At 504, a motor movement command is generated by the motor cortex. Thus, the neural activity at 504 represents a motor movement command. The controller triggers stimulation of the spinal cord at 515 in response to detecting the motor cortex generated motor movement command. In particular, the controller detects the motor cortex generated motor movement command based on the neural activity monitored in the absence of stimulation (plot 510). Thus, plots 501 and 503 at 510 represent the neural activity monitored while not stimulating the spinal cord. The controller then uses this recorded neural activity to determine when to deliver the electrical stimulation during the second phase of the calibration at 512. Thus, the controller may generate an initial motor movement command model (using algorithms such as algorithm 153 shown in FIG. 1) based on monitored neural activity and motor events over repeated cycles of the motor task in the absence of stimulation at 510.

In response to stimulation, a neural response signal (e.g., effects of stimulation on neural activity) is observed during 506. As depicted in graph 500, the neural activity in plots 501 and 503 differ from one another during 504 and different during 506. Thus, observing neural activity recorded on both channels (plots 501 and 503) the neural activity is different when stimulation is delivered at 504, than when it is not at 506.

The controller may monitor the neural response signal during 506 in plot 501 following stimulation at 515 and adjust stimulation of the spinal cord based on the motor movement command model. Once the neural response signal is no longer detected, the controller may trigger stimulation of the spinal cord based on the motor movement command model. At 508, the controller monitors neural activity and the likelihood of a motor event that triggers the stimulation, as calculated by the motor movement command model, has not passed a threshold. Thus, at 508, stimulation by the stimulation device is not delivered to the spinal cord. Later at 504, the motor movement command model calculates the likelihood of a motor event that triggers the stimulation, which passes the threshold at 513. In response to the likelihood of a motor event passing the threshold, the controller triggers stimulation of the spinal cord at 515.

The controller thus monitors neural activity in the absence of stimulation (during 510) and presence of stimulation (during 512) and generates a motor movement command model based on the motor cortex activity monitored during both the absence and presence of stimulation. In particular, motor cortex activity observed during generation of the motor movement command is monitored in the presence and absence of stimulation. In this way, neural activity associated with generation of the motor movement command may be learned during calibration. By calibration a new motor movement command model based on the neural activity and motor events observed both in presence and absence of stimulation, the likelihood of stimulating the spinal cord at the time the stimulation is not desired and the likelihood of not stimulation when it would otherwise be desired, all due to neural activity that results from stimulation, may be reduced.

In this way, during calibration of a neuroprosthetic device, motor cortex activity may be monitored via output from a neurosensor during repeated attempts to perform a desired motor movement (e.g., stepping). Execution of the motor movement may be induced and/or assisted via one or more assisting devices during the calibration. Electrical stimulation may be delivered to the spinal cord at a desired instance. For example, the desired instance to stimulate may be during or immediately following generation of a motor movement command signal. The motor movement command signal may be generated by the motor cortex and may command for execution of the desired motor movement. Thus, the desired instance to stimulate is determined based on neural activity monitored while execution of the desired motor movement is attempted. As such, the desired instance to stimulate may be associated with a distinct neural activity pattern that may comprise the motor movement command signal. During calibration therefore, motor cortex activity is monitored and recorded during and after delivery of the electrical stimulation.

After calibration, execution of the motor movement is induced and/or assisted while the motor movement is attempted. Execution of the motor movement may be induced and/or assisted via one or more assisting devices such as a harness, treadmill, etc., and electrical stimulation is delivered to promote movement recovery. The delivery timing of the electrical stimulation may be determined by detecting the motor events from the neural activity using the motor movement command model calibrated from previously monitored neural activity and motor events. In particular, electrical stimulation may be delivered when the motor movement command model determines that, based on the current neural activity, there is high likelihood of a motor command to execute a motor event that is associated with the desired instance to stimulate. By monitoring neural activity during attempted execution of the motor movement while stimulation is delivered, a more accurate motor movement command model may be determined.

In this way, stimulation of a spinal cord may be more accurately triggered such that motor movement recovery is increased relative to approaches that do not account for the effects of stimulation on neural activity. That is, closed-loop control of spinal cord stimulation based on neural activity may rely on appropriate timing of the stimulation and coordination with brain generated motor movement commands in order to effectively promote motor movement recovery. However, when stimulating the spinal cord, neural activity following the stimulation may be affected by the stimulation. By generating a motor movement command model that can identify motor commands from neural activity both in presence and absence of stimulation effects on the neural activity, stimulation that would be triggered under closed-loop control absent such calibration, may be avoided. Thus, instances of undesirable stimulation and/or overstimulation of the spinal cord may be reduced and/or avoided, resulting in increased motor movement recovery. Furthermore, instances where the stimulation would be desired, but was not initiated due to stimulation effects on the neural activity, may also be avoided, resulting in further increased motor movement recovery.

Thus, a technical effect of reducing electrical stimulation misfires of a spinal cord is achieved by monitoring neural activity during attempted execution of the motor movement while stimulation is delivered. Effects of the stimulation on neural activity may thereby be accounted for. The electrical stimulation may be delivered to the spinal cord at a desired instance during a motor event based on neural activity. The desired instance to stimulate may be determined based on a particular neural activity pattern (e.g., neural spiking pattern) that repeatedly occurs at a given phase or instance during a motor movement. In particular, the neural activity pattern may be a commanded motor movement command that commands for contraction of certain muscles. Thus, the stimulation may be delivered in coordination with a commanded motor movement generated by the brain. In this way, the stimulation may be delivered in conjunction with the brain generated motor movement command to facilitate execution of the motor movement.

However, the electrical stimulation misfire may be an electrical stimulation that is triggered after the electrical stimulation delivered at the desired instance due to the stimulation effect on the neural activity. Specifically, the electrical stimulation misfire may be triggered under closed-loop control because the neural activity resulting from the initial stimulation at the desired instance, may closely resemble neural activity associated with the desired instance to stimulate. The electrical stimulation misfire may have undesirable results, because it may impede or inhibit execution of the motor movement, due to its inaccurate timing.

That is, electrical stimulation, when not delivered at the desired instance during execution of the motor movement, may have adverse effects on motor movement recovery. Furthermore, even if the effects of such mistimed stimulation are positive, albeit not as positive as they could be if the stimulation was timed appropriately, the neural responses to such mistimed stimulation may lead to further, larger loss of temporal accuracy that will further deteriorate the positive effects of the stimulation. By learning how the monitored neural activity corresponding to desired motor movements at which the stimulation is desirable both in presence and absence of stimulation, electrical stimulation misfires may be reduced and/or avoided, leading to increased facilitation of motor movement functionality.

As one embodiment, a method comprises, during a first mode, monitoring motor cortex activity and motor events while not stimulating one or more nerve fibers, during a second mode stimulating the one or more nerve fibers, and monitoring motor cortex activity and motor events during and after stimulating the one or more nerve fibers, and generating a motor movement command model that detects motor events from motor cortex activity during attempted execution of a motor event based on the motor cortex activity monitored during both the first and second modes. In a first example of the method, the second mode is executed after the first mode. A second example of the method optionally includes the first example and further includes wherein the motor event is performed at least once during each of the first and second modes. A third example of the method optionally includes one or more of the first and second examples, and further includes synchronizing the monitored motor cortex activity with the motor events. A fourth example of the method optionally includes one or more of the first, second, and third examples, and further includes wherein during the first mode, motor cortex activity is monitored for a first selected number of repetitions of the motor event, and then during the second mode, motor cortex activity is monitored for a second selected number of repetitions of the motor event. A fifth example of the method optionally includes one or more of the first, second, third, and fourth examples, and further includes wherein during the first mode the method further comprises, generating an initial motor movement command model that detects motor events from motor cortex activity while the one or more nerve fibers are not stimulated based on the monitored motor cortex activity from the first mode, and where the generating the motor movement command model comprises modifying the initial motor movement command model generated during the first mode, based on the motor cortex activity and motor events monitored during the second mode. A sixth example of the method optionally includes one or more of the first, second, third, fourth, and fifth examples, and further includes during the second mode, identifying a neural response signal based on the motor cortex activity monitored during and after the stimulating the one or more nerve fibers, the neural response signal generated in response to the stimulating of the one or more nerve fibers. A seventh example of the method optionally includes one or more of the first, second, third, fourth, fifth, and sixth examples, and further includes wherein the stimulating the one or more nerve fibers is performed only after the neural response signal from a most recent stimulation of the one or more nerve fibers has terminated. An eighth example of the method optionally includes one or more of the first, second, third, fourth, fifth, sixth, and seventh examples, and further includes wherein the stimulating the one or more nerve fibers comprises electrically pulsing the one or more nerve fibers. A ninth example of the method optionally includes one or more of the first, second, third, fourth, fifth, sixth, seventh, and eighth examples, and further includes wherein the stimulating the one or more nerve fibers during the second mode comprises stimulating the one or more nerve fibers at least twice. A tenth example of the method optionally includes one or more of the first, second, third, fourth, fifth, sixth, seventh, eighth, and ninth examples, and further includes wherein the stimulating the one or more nerve fibers comprises stimulating the one or more nerve fibers at a desired instance during execution of a motor event, where the desired instance is determined based on neural activity.

In another representation, a method comprises, while monitoring motor cortex activity during attempted execution of a desired motor movement, electrically stimulating a nerve fiber at a desired instance following a motor movement command, and while inducing execution of the desired motor movement, electrically stimulating the nerve fiber under closed-loop control based on current motor cortex activity and the monitored motor cortex activity. In a first example of the method, the motor movement command is generated by a motor cortex and commands for execution of the desired motor movement. A second example of the method optionally includes the first example and further includes wherein the desired motor movement comprises stepping, and where inducing execution of the stepping comprises assisting the stepping via one or more of a physiotherapists or other caretaker, walker, crutches, cane, gait trainer, prosthesis, exoskeleton, treadmill, and body weight support system with a harness. A third example of the method optionally includes one or more of the first and second examples, and further includes wherein the electrically stimulating the nerve fiber under closed-loop control comprises determining when to deliver the electrical stimulation based on a comparison of the current motor cortex activity to the monitored motor cortex activity. A fourth example of the method optionally includes one or more of the first, second, and third examples, and further comprises generating a motor movement command model based on the previously monitored motor events and motor cortex activity, the motor movement command model comprising a prediction of a motor event from the current motor cortex activity that will occur while the user attempts execution of the desired motor movement. A fifth example of the method optionally includes one or more of the first, second, third, and fourth examples, and further includes wherein the electrically stimulating the nerve fiber under closed-loop control comprises determining a likelihood that the desired instance is occurring based on the current neural activity, and initiating the electrical stimulation in response to the likelihood increasing above a threshold.

In another representation, a method comprises generating a motor movement command model based on neural activity monitored during one or more first repetitions of a motor event, electrically stimulating a nerve fiber during one or more second repetitions of the motor event, updating the motor movement command model based on neural activity monitored during the one or more second repetitions, and electrically stimulating the nerve fiber based on the updated motor movement command model. In a first example of the method, the nerve fiber is not stimulated during the one or more first repetitions of the motor event. A second example of the method optionally includes the first example and further includes wherein the neural activity comprises neural activity patterns that are expected during attempted execution of the motor event. A third example of the method optionally includes one or more of the first and second examples, and further includes synchronizing the neural activity with the one or more first repetitions of the motor event. A fourth example of the method optionally includes one or more of the first, second, and third examples, and further includes wherein the updating the neural activity profile comprises modifying the neural activity profile based on a difference between the neural activity profile and the neural activity monitored during the one or more second repetitions of the motor event. A fifth example of the method optionally includes one or more of the first, second, third, and fourth examples, and further includes wherein the electrically stimulating the nerve fiber based on the updated neural activity profile comprises closed loop controlling the stimulating based on a difference between current neural activity and the updated neural activity profile. A sixth example of the method optionally includes one or more of the first, second, third, fourth, and fifth examples, and further includes wherein the closed loop controlling the stimulating comprises determining a likelihood that the desired instance is occurring based on the current neural activity using the updated motor movement command model, and initiating the electrical stimulation in response to the likelihood increasing above a threshold.

In yet another representation, a neuroprosthetic system comprises a neurosensor for monitoring neural activity, an electrical stimulator for delivering electrical stimulation to one or more nerve fibers, and a controller in communication with the neurosensor and electrical stimulator, the controller including computer readable instruction stored in non-transitory memory for triggering electrical stimulation events based on neural activity data received from the neurosensor, generating a motor movement command model to detect motor events from the current neural activity calibrated from prior synchronized recordings of motor events and neural activity in the presence and absence of stimulation. In a first example of the neuroprosthetic system, the neurosensor comprises one or more of an electrode array, EEG, iEEG, fMRI, electrocorticogram, NIRS, glass pipette electrode, one or two photon excitation imaging with calcium indicators, neural activity recorded using voltage sensitive dyes, neural dust, tetrode array, wire electrodes, and patch clamping.

In another representation, a method for closed-loop operating a stimulator of a neuroprosthetic, the method comprises determining when to activate the stimulator to deliver stimulation based on a likelihood calculated by a motor movement command model from the current neural activity received from a neurosensor, and a motor movement command model that accounts for changes in neural activity resulting from delivery of stimulation, and delivering the stimulation when a likelihood that the current neural activity reflects a desired instance to stimulate increases above a threshold. The method may optionally further include wherein the desired instance to stimulate is during, or immediately after generation of a motor movement command by a motor cortex, the motor movement command comprising a command for execution of a desired motor movement In another representation, a method may comprise electrically stimulating a spinal cord during one or more first repetitions of a motor event, projecting the currently recorded neural activity into a subspace that maintains the distinction between neural activity related to different motor movements desired to be followed by stimulation and other neural activity unrelated to those movements, all in absence and presence of stimulation and its effects on the neural activity, determining whether the likelihood that such projected neural activity resembles the projected patterns of neural activities that correspond to one of the motor movements desired to be followed by stimulation crosses a set threshold, and, in the case that the threshold has been crossed, stimulating the spinal cord after the one or more first repetitions of the motor event based on the neural activity. In a first example of the method, the method may further comprise, not electrically stimulating the spinal cord during one or more second repetitions of the motor event before electrically stimulating the spinal cord during the one or more first repetitions of the motor event. A second example of the method optionally includes the first example and may further include wherein the identifying the stimulation response signal comprises comparing neural activity during the one or more first repetitions of the motor event to neural activity during the one or more second repetitions of the motor event. A third example of the method optionally includes one or more of the first and second examples, and may further include electrically stimulating the spinal cord at least twice during each of the one or more first repetitions of the motor event, where the timing of the at least two stimulations during each of the one or more first repetitions of the motor event is the same for all of the one or more first repetitions of the motor event. A fourth example of the method optionally includes one or more of the first through third examples, and may further include identifying neural response signals for each of at least two stimulations, where the neural response signals for each of at least two stimulations are unique. A fifth example of the method optionally includes one or more of the first, second, third, and fourth examples, and may further include wherein the electrically stimulating the spinal cord occurs only after the stimulation response signal from a most recent electrical stimulation of the spinal cord has ended. The method of claim 21, wherein the electrically stimulating the spinal cord comprises electrically stimulating the spinal cord after a duration since a most recent electrical stimulation of the spinal cord. A sixth example of the method optionally includes one or more of the first, second, third, fourth, and fifth examples, and may further include wherein the adjusting the electrical stimulation comprises adjusting when the spinal cord is stimulated during the one or more repetitions based on a comparison of the neural activity data to a predicted neural activity model, the model generated calibrated based on the identified stimulation response signal.

In another representation, a method may comprise determining a neural activity profile associated with a motor movement (e.g., gait cycle) while not stimulating one or more nerve fibers based on motor cortex activity recorded during the motor movement electrically stimulating the one or more nerve fibers, learning a stimulation response profile associated with the electrical stimulation, and adjusting the neural activity profile based on the stimulation response profile.

In another representation, a method may comprise during a first mode, monitoring motor cortex activity while not stimulating one or more nerve fibers, during a second mode electrically stimulating the one or more nerve fibers, and monitoring motor cortex activity while the electrical stimulation is affecting motor cortex activity, and determining a stimulation protocol based on the monitored motor cortex activity from both the first and second modes.

In another representation, a method for calibrating a neuroprosthetic device may comprise learning a neural activity pattern coding for a motor movement while not stimulating one or more nerve fibers used for performing the motor movement, after learning the neural activity pattern stimulating the one or more nerve fibers, and monitoring neural activity during the stimulating and for a duration thereafter, and determining a neural activity model based on both the neural activity pattern and the monitored neural activity.

In another representation, a method may comprise calibrating a neuroprosthetic device by first, generating a motor movement command model designed to detect a motor event while not stimulating one or more nerve fibers involved in executing the motor movement, then monitoring motor cortex activity while electrically stimulating the one or more nerve fibers, and then generating a motor movement command model based on motor cortex activity monitored during both of the stimulating and not stimulating of the one or more nerve fibers.

In another representation, a method may comprise electrically stimulating a spinal cord, correlating the electrical stimulation to changes in neural activity in a motor cortex, filtering neural activity data based on the correlation, and adjusting electrical stimulation to the spinal cord based on the filtered neural activity data.

In another representation, a method may comprise determining a desired instance to stimulate a spinal cord based on neural activity, modifying the desired instance based on changes in neural activity resulting from electrical stimulation to a spinal cord, and electrically stimulating the spinal cord at the modified desired instance.

In another representation, a method may comprise monitoring motor cortex activity while not stimulating one or more nerve fibers, identifying a motor cortex stimulation response signal based on changes in motor cortex activity during and after stimulation of the one or more nerve fibers, and adjusting a spinal cord stimulation protocol based on the identified stimulation response signal.

In another representation, a method may comprise calibrating a motor movement command model using motor events and neural activity recorded while not stimulating one or more nerve fibers, determining a desired instance to electrically stimulate one or more nerve fibers with respect to the collected motor events, electrically stimulating the one or more nerve fibers at the desired instance, updating the motor movement command model based on motor events and neural activity recorded during the electrical stimulation, and electrically stimulating the one or more nerve fibers based on the updated motor movement command model.

In another representation, a method may comprise electrically stimulating one or more nerve fibers, monitoring neural activity during the electrical stimulation and for a duration thereafter, updating an expected neural activity profile based on a difference between the monitored neural activity and the expected neural activity profile, and adjusting the electrical stimulation (e.g., timing, duration, frequency, burst profile, voltage profile, etc.) based on the updated expected neural activity profile.

In another representation, a method may comprise generating a motor movement command model while not stimulating a nerve fiber, determining a desired instance to electrically stimulate the nerve fiber based on the motor movement command model and the current neural activity, electrically stimulating the nerve fiber at the desired instance, updating the motor movement command model based on motor events and neural activity while stimulating and not stimulating the nerve fiber, and electrically stimulating the nerve fiber based on the updated motor movement command model.

Note that the example control and estimation routines included herein can be used with various neuroprosthetic system configurations. The control methods and routines disclosed herein may be stored as executable instructions in non-transitory memory and may be carried out by the control system including the controller in combination with the various sensors, actuators, and other hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the control system, where the described actions are carried out by executing the instructions in a system including the stimulator in combination with the electronic controller.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method comprising:
    during a first mode, monitoring motor events and motor cortex activity while not stimulating one or more nerve fibers;
    during a second mode:
        stimulating the one or more nerve fibers; and
        monitoring motor events and motor cortex activity during and after stimulating the one or more nerve fibers; and
        generating a motor movement command model that predicts motor movement commands during attempted execution of a motor event based on the motor cortex activity monitored during both the first and second modes;
    wherein during the first mode the method further comprises, generating an initial motor movement command model that predicts motor movement commands from motor cortex activity during the motor event while the one or more nerve fibers are not stimulated based on the monitored motor cortex activity from the first mode, and where the generating the motor movement command model comprises modifying the initial motor movement command model generated during the first mode, based on the motor cortex activity monitored during the second mode.

2. The method of claim 1, wherein the second mode is executed after the first mode.

3. The method of claim 1, wherein the motor event is performed at least once during each of the first and second modes.

4. The method of claim 3, further comprising synchronizing the monitored motor cortex activity with the motor events, and where the motor movement commands comprise motor cortex generated commands for executing the motor event.

5. The method of claim 1, further comprising, during the second mode, identifying a neural response signal based on the motor cortex activity monitored during and after the stimulating of the one or more nerve fibers, the neural response signal generated in response to the stimulating of the one or more nerve fibers.

6. The method of claim 5, wherein the stimulating of the one or more nerve fibers is performed only after the neural response signal from a most recent stimulation of the one or more nerve fibers has terminated.

7. The method of claim 1, wherein the stimulating of the one or more nerve fibers comprises electrically pulsing the one or more nerve fibers.

8. The method of claim 1, wherein the stimulating of the one or more nerve fibers during the second mode comprises stimulating the one or more nerve fibers at least twice.

9. The method of claim 1, wherein the stimulating of the one or more nerve fibers comprises stimulating the one or more nerve fibers at a desired instance during execution of a motor event, where the desired instance is determined based on neural activity.

10. A method comprising:
while monitoring motor cortex activity during attempted execution of a desired motor movement, electrically stimulating a nerve fiber at a desired instance following a motor movement command; and
while inducing execution of the desired motor movement, electrically stimulating the nerve fiber under closed-loop control based on current motor cortex activity and the monitored motor cortex activity;
wherein the desired motor movement comprises stepping, and where inducing execution of the stepping comprises assisting the stepping via one or more of a physiotherapists or other caretaker, walker, crutches, cane, gait trainer, prosthesis, exoskeleton, treadmill, and body weight support system with a harness.

11. The method of claim 10, wherein the motor movement command is generated by a motor cortex and commands for execution of the desired motor movement.

12. The method of claim 10, wherein the electrically stimulating the nerve fiber under closed-loop control comprises determining when to deliver the electrical stimulation based on the output of a motor movement command model using processed current motor cortex activity that is indicative of current neural activity.

13. A method for closed-loop operating a stimulator of a neuroprosthetic, the method comprising:
determining when to activate the stimulator to deliver stimulation based on output of a motor movement command model calculated from current neural activity received from a neurosensor, and the motor movement command model accounts for effects of stimulation on the neural activity, wherein the motor movement command model is calibrated based on previously recorded and synchronized motor events and neural activity, the motor movement command model comprising a prediction of motor movement commands from the current neural activity that will occur while inducing execution of the desired motor movement; and
delivering the stimulation when a likelihood of a desired instance to stimulate increases above a threshold, as calculated by the motor movement command model from the current neural activity.

14. The method of claim 13, wherein the desired instance to stimulate is during, or immediately after, generation of a motor movement command by a motor cortex, the motor movement command comprising a command for execution of the desired motor movement.

15. A method comprising:
during a first mode, monitoring motor events and motor cortex activity while not stimulating one or more nerve fibers;
during a second mode:
stimulating the one or more nerve fibers; and
monitoring motor events and motor cortex activity during and after stimulating the one or more nerve fibers; and
generating a motor movement command model that predicts motor movement commands during attempted execution of a motor event based on the motor cortex activity monitored during both the first and second modes;
wherein the motor event is performed at least once during each of the first and second modes;
wherein during the first mode, motor cortex activity is monitored for a first selected number of repetitions of the motor event, and then during the second mode, motor cortex activity is monitored for a second selected number of repetitions of the motor event.

16. A method comprising:
while monitoring motor cortex activity during attempted execution of a desired motor movement, electrically stimulating a nerve fiber at a desired instance following a motor movement command; and
while inducing execution of the desired motor movement, electrically stimulating the nerve fiber under closed-loop control based on current motor cortex activity and the monitored motor cortex activity; and
calibrating a motor movement command model based on previously recorded and synchronized motor events and neural activity, the motor movement command model comprising a prediction of motor movement commands from current neural activity that will occur while inducing execution of the desired motor movement.

17. A method comprising:
while monitoring motor cortex activity during attempted execution of a desired motor movement, electrically stimulating a nerve fiber at a desired instance following a motor movement command; and
while inducing execution of the desired motor movement, electrically stimulating the nerve fiber under closed-loop control based on current motor cortex activity and the monitored motor cortex activity;
wherein the electrically stimulating the nerve fiber under closed-loop control comprises determining a likelihood that the desired instance is occurring, that likelihood being the likelihood that motor movement command is formed, as calculated by the motor movement command model from the current neural activity, and initiating the electrical stimulation in response to the likelihood increasing above a threshold.

* * * * *